United States Patent
Imai

(10) Patent No.: US 7,522,696 B2
(45) Date of Patent: Apr. 21, 2009

(54) X-RAY CT APPARATUS

(75) Inventor: Yasuhiro Imai, Tokyo (JP)

(73) Assignee: General Electric Company, Schenectady, NY (US)

( * ) Notice: Subject to any disclaimer, the term of this patent is extended or adjusted under 35 U.S.C. 154(b) by 112 days.

(21) Appl. No.: 11/620,627

(22) Filed: Jan. 5, 2007

(65) Prior Publication Data

US 2007/0237286 A1 Oct. 11, 2007

(30) Foreign Application Priority Data

Apr. 6, 2006 (JP) .............................. 2006-105749

(51) Int. Cl.
G01N 23/083 (2006.01)
H05G 1/62 (2006.01)

(52) U.S. Cl. .......................................... 378/8; 378/15

(58) Field of Classification Search ..................... 378/8, 378/15, 95; 600/428
See application file for complete search history.

(56) References Cited

U.S. PATENT DOCUMENTS

| | | | |
|---|---|---|---|
| 5,271,055 A | 12/1993 | Hsieh et al. | |
| 5,708,691 A | 1/1998 | Zmora | |
| 5,825,842 A | 10/1998 | Taguchi | |
| 5,828,718 A | 10/1998 | Ruth et al. | |
| 5,848,117 A | 12/1998 | Urchuk et al. | |
| 5,966,422 A * | 10/1999 | Dafni et al. ................. | 378/9 |
| 5,974,108 A | 10/1999 | Taguchi et al. | |
| 6,072,851 A | 6/2000 | Sivers | |
| 6,118,839 A | 9/2000 | Dafni et al. | |
| 6,154,516 A | 11/2000 | Heuscher et al. | |
| 6,185,275 B1 | 2/2001 | Toth et al. | |
| 6,275,560 B1 | 8/2001 | Blake et al. | |
| 6,466,640 B1 | 10/2002 | Taguchi | |
| 6,470,066 B2 * | 10/2002 | Takagi et al. .................. | 378/8 |
| 6,708,052 B1 * | 3/2004 | Mao et al. .................. | 600/407 |
| 6,760,399 B2 * | 7/2004 | Malamud ...................... | 378/9 |
| 6,763,082 B2 * | 7/2004 | Ozaki ............................ | 378/8 |
| 6,865,248 B1 * | 3/2005 | Rasche et al. .................. | 378/8 |

(Continued)

FOREIGN PATENT DOCUMENTS

JP 2004-208715 7/2004 ....................... 6/3

OTHER PUBLICATIONS

Japanese search report from foreign parent application.

Primary Examiner—Edward J Glick
Assistant Examiner—Thomas R Artman
(74) Attorney, Agent, or Firm—Fisher Patent Group, LLC; Thomas M. Fisher

(57) ABSTRACT

An X-ray CT apparatus includes an X-ray data acquisition device for acquiring X-ray projection data transmitted through a subject lying between an X-ray generator and an X-ray detector having a two-dimensional detection plane and detecting X rays in opposition to the X-ray generator, while the X-ray generator and the X-ray detector are being rotated about a center of rotation lying there between; an image reconstructing device for image-reconstructing the acquired projection data; an image display device for displaying the image-reconstructed tomographic image; and an imaging condition setting device for setting various kinds of imaging conditions for tomographic image, wherein the X-ray data acquisition device acquires X-ray projection data in sync with an external sync signal by a helical scan with a predetermined range of the subject with a helical pitch set to 1 or more.

18 Claims, 23 Drawing Sheets

U.S. PATENT DOCUMENTS

| | | | |
|---|---|---|---|
| 6,865,250 B2 * | 3/2005 | Londt et al. | 378/8 |
| 2004/0008819 A1 | 1/2004 | Drummond et al. | 378/162 |
| 2004/0077941 A1 * | 4/2004 | Reddy et al. | 600/428 |
| 2004/0179644 A1 | 9/2004 | Tsuyuki | 378/8 |
| 2005/0089133 A1 | 4/2005 | Tsuyuki | 378/8 |

* cited by examiner (a)

(b)

(a)

(b)

(a)

(b)

(c)

X-RAY CT APPARATUS

CROSS REFERENCE TO RELATED APPLICATIONS

This application claims the benefit of Japanese patent application number 2006-105749 filed Apr. 6, 2006.

BACKGROUND OF THE INVENTION

The present invention relates to an X-ray CT apparatus or a technique for an X-ray CT image photographing or imaging method, which realize cardiac imaging or biological synchronous imaging based on low radiation exposure, high image quality and high-speed photography by an electrocardiographically-synchronized helical scan, variable-pitch helical scan or helical shuttle scan at a medical X-ray CT (Computed Tomography) apparatus.

In an X-ray CT apparatus using a multi-row X-ray detector or an X-ray CT apparatus using a two-dimensional X-ray area detector of a matrix structure typified by a flat panel, the photography of the heart has heretofore been performed by a helical scan electrocardiographically synchronized at a helical pitch made slow by a helical pitch 0.2 or so as shown in FIG. 16. As the technique of photographing or imaging such as a heart by the helical scan, a patent document 1 has been known.

The present imaging method involves a problem in terms of X-ray exposure because of the low helical pitch. Data acquisition in which one segment is defined as fan angles+180° is shown in FIG. 16. However, as in the case in which multi-segment image reconstruction is taken as shown in FIGS. 17 and 18 to adapt to various heartbeats, problems arise even in terms of image quality as in the case of the occurrence of artifacts due to displacements in X-ray projection data between respective segments, the occurrence of banding artifacts in the direction orthogonal to a z direction parallel to an xy plane at a three-dimensional display as shown in FIG. 20, and the like.

[Patent Document 1] Japanese Unexamined Patent Publication No. 2003-164446

Assuming that, for example, an X ray having a beam width of 40 mm is used and imaging is done at a helical pitch 0.2, an imaging area is moved 8 mm per one scan rotation. Therefore, there is a need to carry out imaging corresponding to 15 rotations of a gantry for the purpose of imaging or photographing a heart whose overall length is 12 cm or so. Radiation dose reduction is typically desirable and it is desirable to reduce any X-ray projection data that may be unused in the actual diagnosis exist in large quantities, as well as about an exposed dose equivalent to greater than or equal to 5 times as compared with a conventional scan (axial scan) which enables imaging of 40 mm minutes per rotation of gantry. On the other hand, since a z direction X-ray detector width is not yet sufficient in the normal conventional scan (axial scan), data acquisition per rotation is not capable of covering the whole heart.

Therefore, an object of the present invention is to provide an X-ray CT apparatus capable of realizing the photography or imaging of a heart at a low dosage and a high speed and with good image quality by a helical scan, variable pitch helical scan or helical shuttle scan of the X-ray CT apparatus having a multi-row X-ray detector or a two-dimensional X-ray area detector of matrix structure typified by a flat panel X-ray detector.

BRIEF DESCRIPTION OF THE INVENTION

In a first aspect, the present invention provides an X-ray CT apparatus including an X-ray data acquisition device for acquiring X-ray projection data transmitted through a subject lying between an X-ray generator and an X-ray detector having a two-dimensional detection plane and detecting X rays in opposition to the X-ray generator, while the X-ray generator and the X-ray detector are being rotated about a center of rotation lying therebetween; an image reconstructing device for image-reconstructing the acquired projection data; an image display device for displaying the image-reconstructed tomographic image; and an imaging condition setting device for setting various kinds of imaging conditions for tomographic image, wherein the X-ray data acquisition device acquires X-ray projection data in sync with an external sync signal by a helical scan with a predetermined range of the subject with a helical pitch set to 1 or more.

In another aspect the present invention provides an X-ray CT apparatus including an X-ray data acquisition device for acquiring X-ray projection data transmitted through a subject lying between an X-ray generator and an X-ray deter having a two-dimensional detection plane and detecting X rays in opposition to the X-ray generator, while the X-ray generator and the X-ray deter are being rotated about the center of rotation lying therebetween; an image reconstructing device for image-reconstructing the acquired projection data; an image display device for displaying the image-reconstructed tomographic image; and an imaging condition setting device for setting various imaging conditions for a tomographic image, wherein the X-ray data acquisition device performs X-ray data acquisition with a timing at which a predetermined imaging position in a z direction that is a relative travel direction between the subject and an X-ray data acquisition system including the X-ray generator and the X-ray detector is synchronized with a predetermined phase of an external sync signal, upon imaging a predetermined range of the subject by a helical scan.

In yet another aspect, the present invention provides an X-ray CT apparatus including an X-ray data acquisition device for acquiring X-ray projection data transmitted through a subject lying between an X-ray generator and an X-ray detector having a two-dimensional detection plane and detecting X-rays in opposition to the X-ray generator, while the X-ray generator and the X-ray detector are being rotated about a center of rotation lying therebetween; an image reconstructing device for image-reconstructing the acquired projection data; an image display device for displaying the image-reconstructed tomographic image; and an imaging condition setting device for setting various kinds of imaging conditions for tomographic image, wherein the X-ray data acquisition device includes a first X-ray data acquisition device for performing first X-ray data acquisition based on a first imaging condition defined in such a manner that a predetermined imaging position in a z direction that is a relative travel direction between the subject and an X-ray data acquisition system including the X-ray generator and the X-ray detector is synchronized with a predetermined phase of an external sync signal, upon imaging a predetermined range of the subject by a helical scan, and a second X-ray data acquisition device for performing second X-ray data acquisition based on a second imaging condition defined in such a manner that the predetermined imaging position is more properly synchronized with the predetermined phase of the external sync signal, upon imaging the predetermined range by the helical scan based on the tomographic image obtained by image-reconstructing the X-ray projection data obtained by the first X-ray data acquisition device, and wherein the image reconstructing device image-reconstructs X-ray projection data acquired by the first and second X-ray data acquisition devices.

DETAILED DESCRIPTION OF THE INVENTION

The present invention will hereinafter be explained in further detail by embodiments illustrated in the figures. Incidentally, the present invention is not limited to or by the illustrated embodiments.

Figure 1:
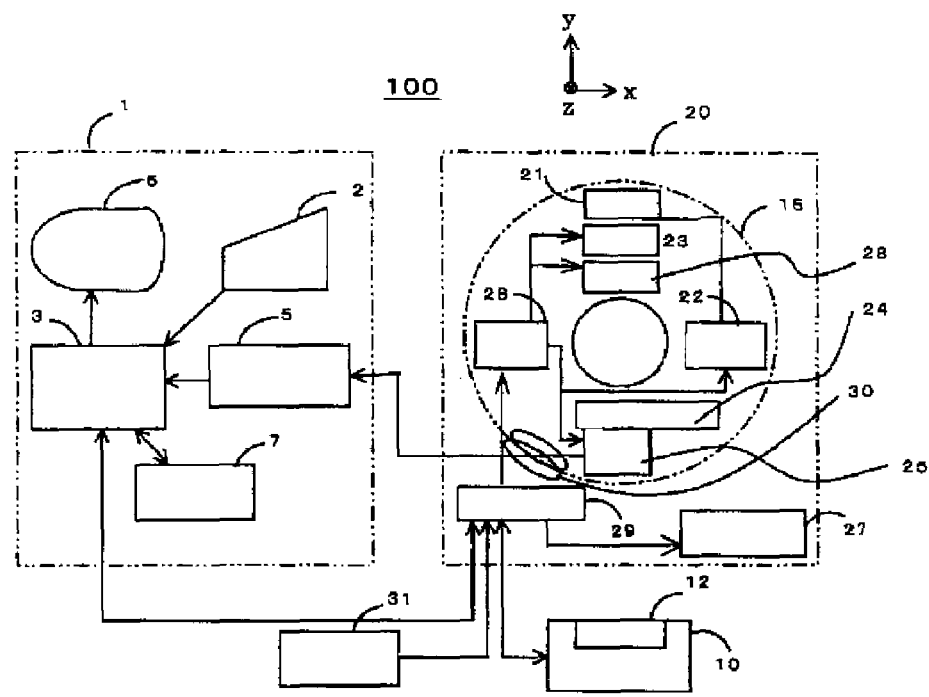
FIG. 1 is a block diagram showing an X-ray CT apparatus according to one embodiment of the present invention

FIG. 1 is a configuration block diagram showing an X-ray CT apparatus according to one embodiment of the present invention. The X-ray CT apparatus 100 is equipped with an operation console 1, an imaging or photographing table 10 and a scan gantry 20.

The operation console 1 includes an input device 2 which accepts an input from an operator, a central processing unit 3 which executes a pre-process, an image reconstructing process, a post-process, etc., a data acquisition buffer 5 which acquires or collects X-ray detector data acquired by the scan gantry 20, a monitor 6 which displays a tomographic image image-reconstructed from projection data obtained by pre-processing the X-ray detector data, and a storage device 7 which stores programs, X-ray detector data, projection data and X-ray tomographic images therein.

Figure 14:
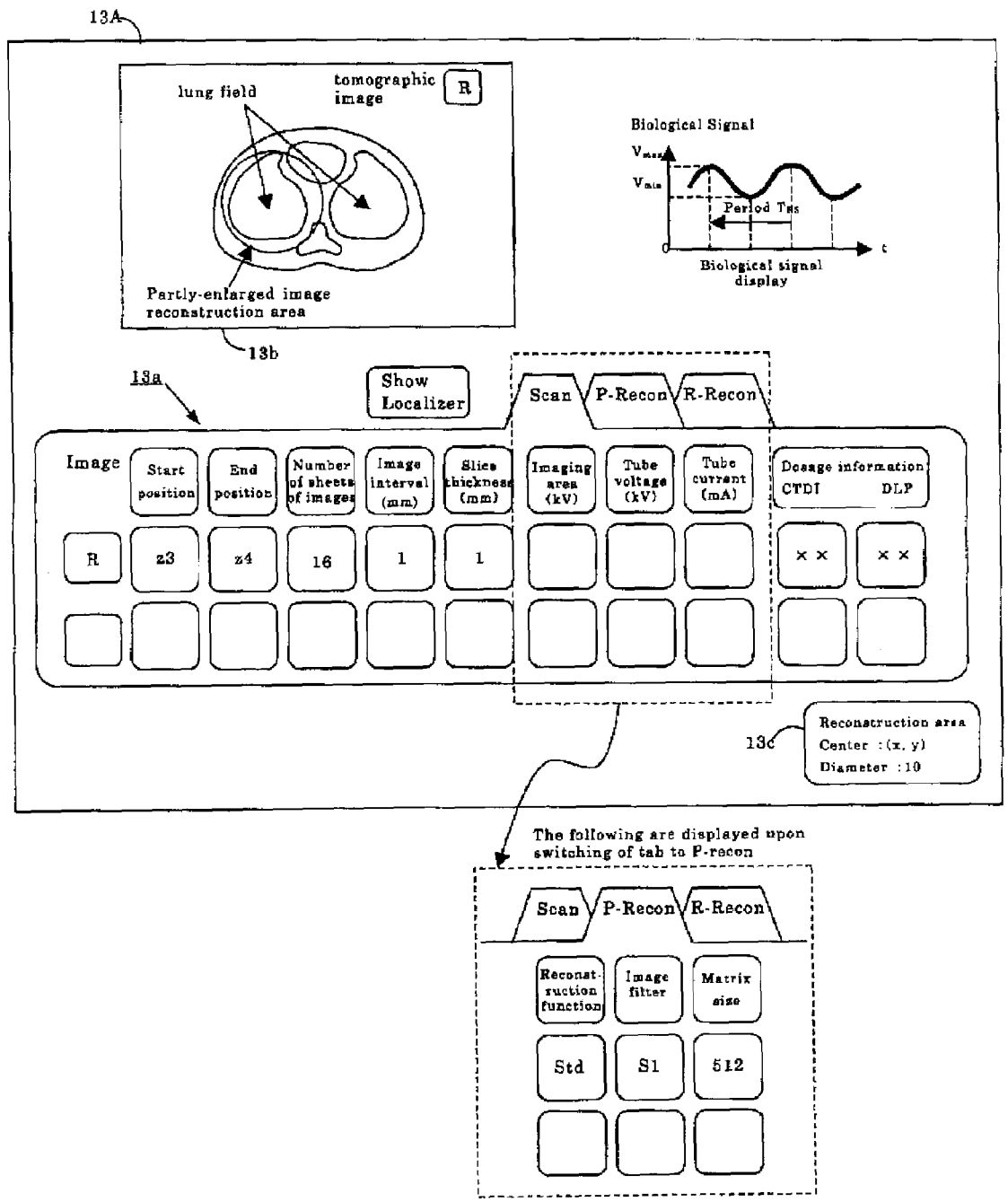
FIG. 14 is a diagram illustrating an imaging or photographing condition input screen of the X-ray CT apparatus.

An input for imaging or photographing conditions is inputted from the input device 2 and stored in the storage device 7. FIG. 14 shows an example of an imaging condition input screen. An input button 13a for performing a predetermined input is displayed on the imaging condition input screen 13A. FIG. 14 illustrates a screen on which a scan tab is being selected. When P-Recon is selected as the tab, an input display is switched as plotted below FIG. 14. A tomographic image 13b is displayed above the input button 13a and a reconstruction area 13c is displayed down below. Biological signals such as a respiratory signal, an electrocardiographic signal, etc. may be displayed as displayed on the upper right side if necessary.

The photographing table 10 includes a cradle 12 that draws and inserts a subject from and into a bore or aperture of the scan gantry 20 with the subject placed thereon. The cradle 12 is elevated and moved linearly on the photographing table by a motor built in the photographing table 10.

The scan gantry 20 includes an X-ray tube 21, an X-ray controller 22, a collimator 23, a beam forming X-ray filter 28, a multi-row X-ray detector 24, a data acquisition system (DAS) 25, a rotating section controller 26 which controls the X-ray tube 21 or the like rotated about a body axis of the subject, and a control controller 29 which swaps control signals or the like with the operation console 1 and the photographing table 10. The beam forming X-ray filter 28 is an X-ray filter configured so as to be thinnest in thickness as viewed in the direction of X rays directed to the center of rotation corresponding to the center of imaging, to increase in thickness toward its peripheral portion and to be able to further absorb the X rays. Therefore, the body surface of the subject whose sectional shape is nearly circular or elliptic can be less exposed to radiation. The scan gantry 20 can be tiled about ±30° or so forward and rearward as viewed in a z direction by a scan gantry tilt controller 27.

The X-ray tube 21 and the multi-row X-ray detector 24 are rotated about the center of rotation IC. Assuming that the vertical direction is a y direction, the horizontal direction is an x direction and the travel direction of each of the table and cradle orthogonal to these is a z direction, the plane at which the X-ray tube 21 and the multi-row X-ray detector 24 are rotated, is an xy plane. The direction in which the cradle 12 is moved, corresponds to the z direction.

An electrocardiograph 31 inputs an electrocardiographic signal of the subject therein. The waveform of the electrocardiographic signal is generally represented as shown in FIG. 22(a). Assuming that a cardiac or heart rate is 75 bpm (beat per minute), a cardiac cycle or period becomes 0.8 seconds and such electrocardiographic waveforms (P wave, QRS wave, T wave and U wave) as shown in the drawing appear within this period. The cardiac atria excites and cont with the timing of the P wave, thereby allowing bloodstream from each of a large vein and a pulmonary vein to flows into the ventricular side. At the timing of its subsequent QRS wave, the cardiac atria simmers down from its excitation and the cardiac ventricle or chamber excites and contracts, thereby squeezing the bloodstream of the cardiac chamber into a main a and a pulmonary artery. At the timing of the subsequent T wave, the cardiac chamber simmers down. And the motion of the heart becomes most gradual at the timing (cardiac phase 75%) of the subsequent U wave. Since the electrocardiograph 31 is connected to the control controller 29, the control controller 29 is capable of performing a scan while a scan operation is being synchronized with the heartbeat.

Figure 2:
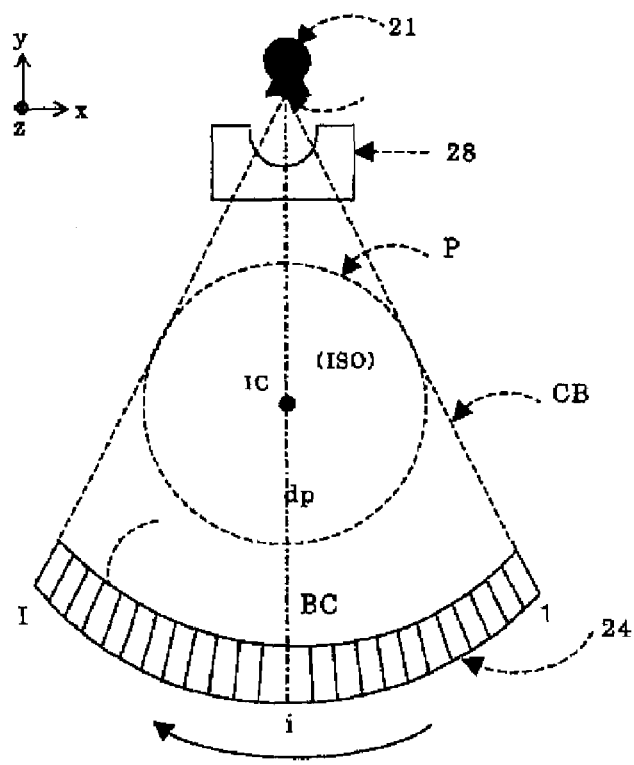
FIG. 2 is an explanatory diagram of an X-ray generator (X-ray tube) and a multi-row X-ray detector as viewed in an xy plane.
Figure 3:
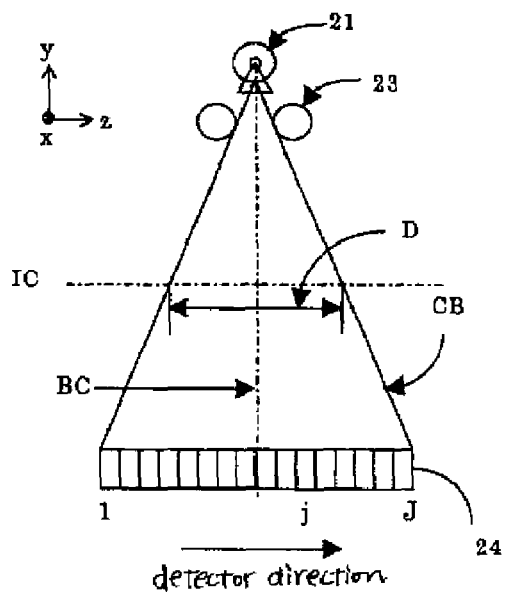
FIG. 3 is an explanatory diagram of the X-ray generator and the multi-row X-ray detector as viewed in a yz plane.

FIG. 2 is a diagram showing a geometrical arrangement or layout of the X-ray tube 21 and the multi-row X-ray detector 24 as viewed from the xy plane. FIG. 3 is a diagram showing a geometrical arrangement or layout of the X-ray tube 21 and the multi-row X-ray detector 24 as viewed from a yz direction. The X-ray tube 21 generates an X-ray beam called a cone beam CB. When the direction of a central axis of the cone beam CB is parallel to the y direction, this is defined as a view angle 0°.

The multi-row X-ray detector 24 has X-ray detector rows corresponding to J rows, for example, 256 rows as viewed in the z direction. Each of the X-ray detector rows has X-ray detector channels corresponding to I channels, for example, 1024 channels as viewed in a channel direction.

In FIG. 2, an X-ray beam emitted from the X-ray focal point of the X-ray tube 21 is set such that more X rays are irradiated at the center of a reconstruction area P by the beam forming X-ray filter 28 and less X rays are irradiated at a peripheral portion thereof thereby. After X-ray dosage has been spatially controlled in this way, the X rays are absorbed into a subject existing inside the reconstruction area P, and the penetrated X rays are acquired or collected by the multi-row X-ray detector 24 as X-ray detector data.

In FIG. 3, the X-ray beam emitted from the X-ray focal point of the X-ray tube 21 is controlled in the direction of slice thickness of a tomographic image by the X-ray collimator 23. That is, the X-ray beam is controlled in such a manner that an X-ray beam width becomes D at the center or central axis of rotation IC. The X-rays are absorbed into the subject existing in the neighborhood of the central axis of rotation IC, and the penetrated X-rays are acquired by the multi-row X-ray detector 24 as X-ray detector data The X-rays are applied to the subject and acquired projection data are A/D converted by the data acquisition system (DAS) 25 from the multi-row X-ray detector 24, which in turn are inputted to the data acquisition buffer 5 via a slip ring 30. The data inputted to the data acquisition buffer 5 are processed by the central processing unit 3 in accordance with the corresponding program stored in the storage device 7, so that the data are image-reconstructed as a tomographic image, followed by being displayed on the monitor 6. Incidentally, although the multi-row X-ray detector 24 is applied in the present embodiment, a two-dimensional X-ray area detector of a matrix structure typified by a flat panel X-ray detector can also be applied, or a one-row type X-ray detector can be applied.

(Operation Flowchart of X-ray CT Apparatus)

Figure 4:
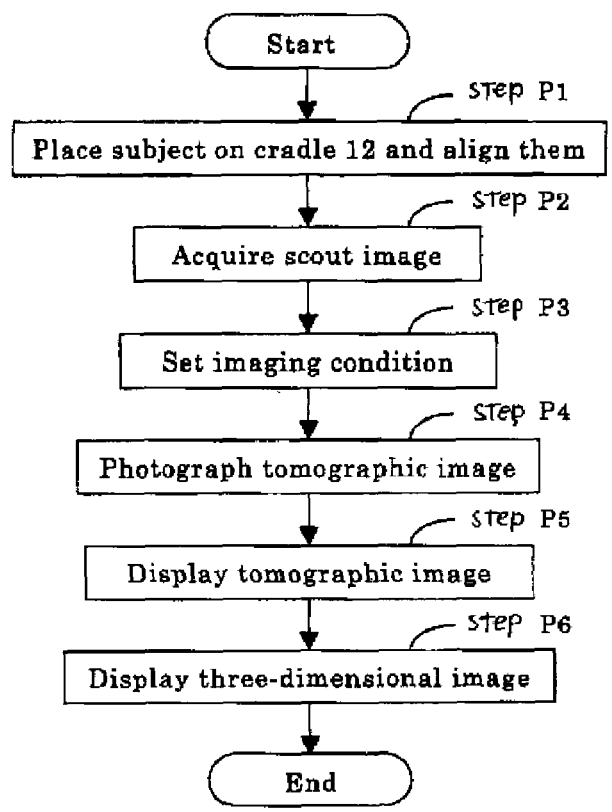
FIG. 4 is a flowchart illustrating the flow of subject photography.

FIG. 4 is a flowchart showing the rough outline of operation of the X-ray CT apparatus according to the present embodiment.

At Step P1, a subject is placed on its corresponding cradle 12 and their alignment is performed. In the subject placed on the cradle 12, a slice light central position of the scan gantry 20 is aligned with a reference point of its each portion or region.

At Step P2, scout image (called also "scano image or X-ray penetrated image") acquisition is performed. The scout image can be normally imaged or photographed at 0° and 90°. Only the 90° scout image might be taken depending upon the region as in the case of a head, for example. The operation of fixing the X-ray tube 21 and the multi-row X-ray detector 24 and effecting data acquisition of X-ray detector data while the cradle 12 is being linearly moved, is performed upon scout image photography. The details of the photography of the scout image will be explained later in FIG. 5.

At Step P3, an imaging condition setting is performed while the position and size of a tomographic image to be photographed on the scout image is being displayed. The present embodiment has a plurality of scan patterns such as a conventional scan (axial scan), a helical scan, a variable pitch helical scan, a helical shuttle scan, etc. The conventional scan is a scan method of rotating the X-ray tube 21 and the multi-row X-ray detector 24 each time the cradle 12 is moved at predetermined intervals in a z-axis direction, thereby acquiring projection data. The helical scan is an photographing or imaging method of moving the cradle 12 at a constant speed while the data acquisition system constituted of the X-ray tube 21 and the multi-row X-ray detector 24 is being rotated, thereby acquiring projection data. The variable pitch helical scan is an imaging method of varying the speed or velocity of the cradle 12 while the data acquisition system constituted of the X-ray tube 21 and the multi-row X-ray detector 24 is being rotated in a manner similar to the helical scan, thereby acquiring projection data. The helical shuttle scan is a scan method of accelerating/decelerating the cradle 12 while the data acquisition system constituted of the X-ray tube 21 and the multi-row X-ray detector 24 is being rotated in a manner similar to the helical scan, thereby to reciprocate it in the positive or negative direction of a z axis to acquire projection data. When these plural photographies are set information about the whole X-ray dosage corresponding to one time is displayed. When the number of rotations or time is inputted upon a cine scan, information about X-ray dosage corresponding to the inputted number of rotations or time at its region of interest is displayed.

At Step P4, a tomographic image is photographed. The details of the tomographic image photography and its image reconstruction will be explained later in FIG. 5.

At Step P5, the image-reconstructed tomographic image is displayed.

Figure 15:
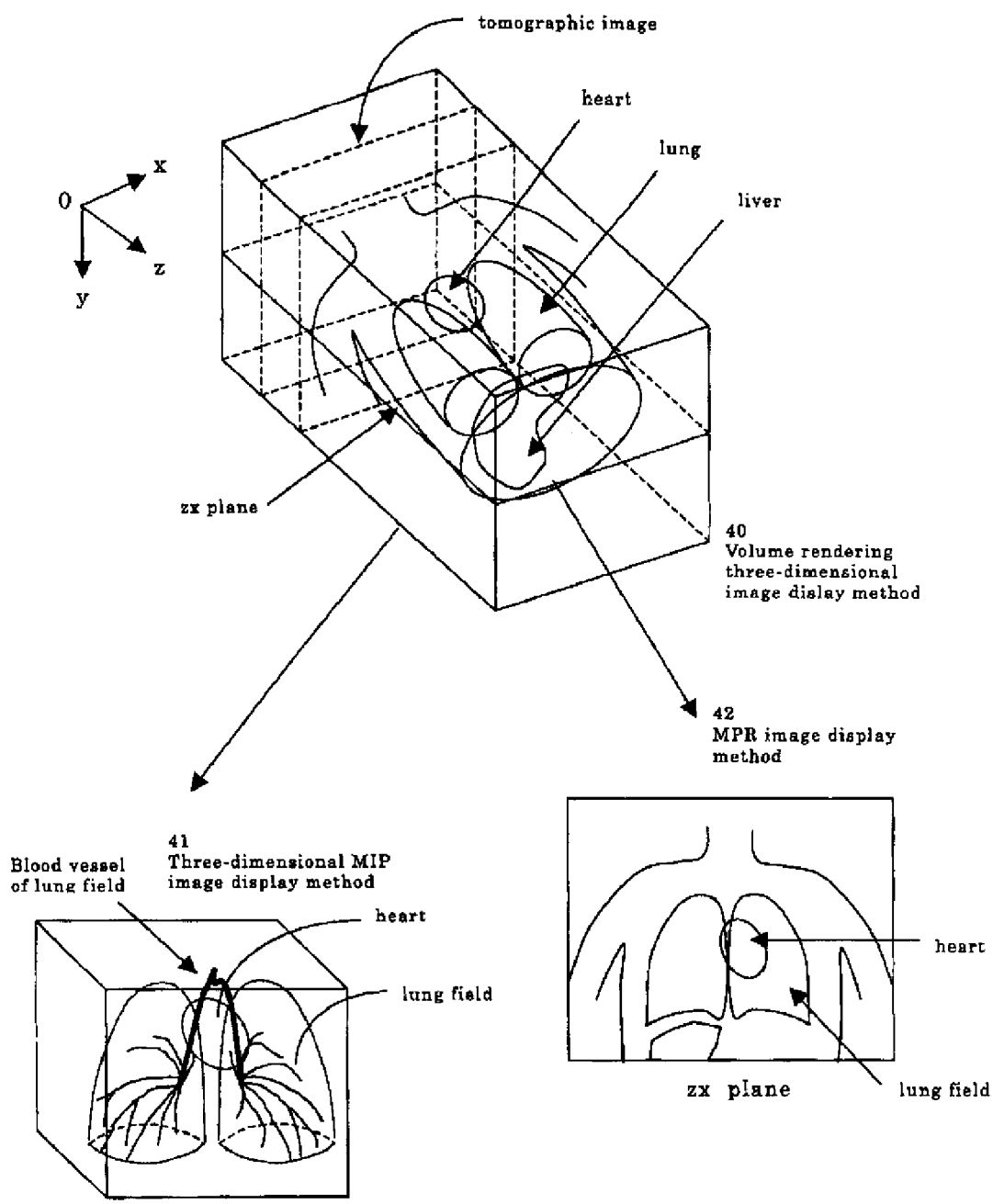
FIG. 15 is a diagram depicting examples of a volume rendering three-dimensional image display method, an MPR image display method and a three-dimensional MIP image display method.

At Step P6, a three-dimensional image display is performed as shown in FIG. 15 using a tomographic image continuously photographed in the z direction as a three-dimensional image.

As three-dimensional image display methods, a volume rendering three-dimensional image display method 40, a three-dimensional MIP (Maximum Intensity Projection) image display method 41, an MPR (Multi Plain Reformat) image display method 42 and a three-dimensional reprojection image display method are shown in FIG. 15. The various image display methods can be used properly according to diagnostic applications.

(Operation Flow Chart for Tomographic Image Photography and Scout Image Photography)

Figure 5:
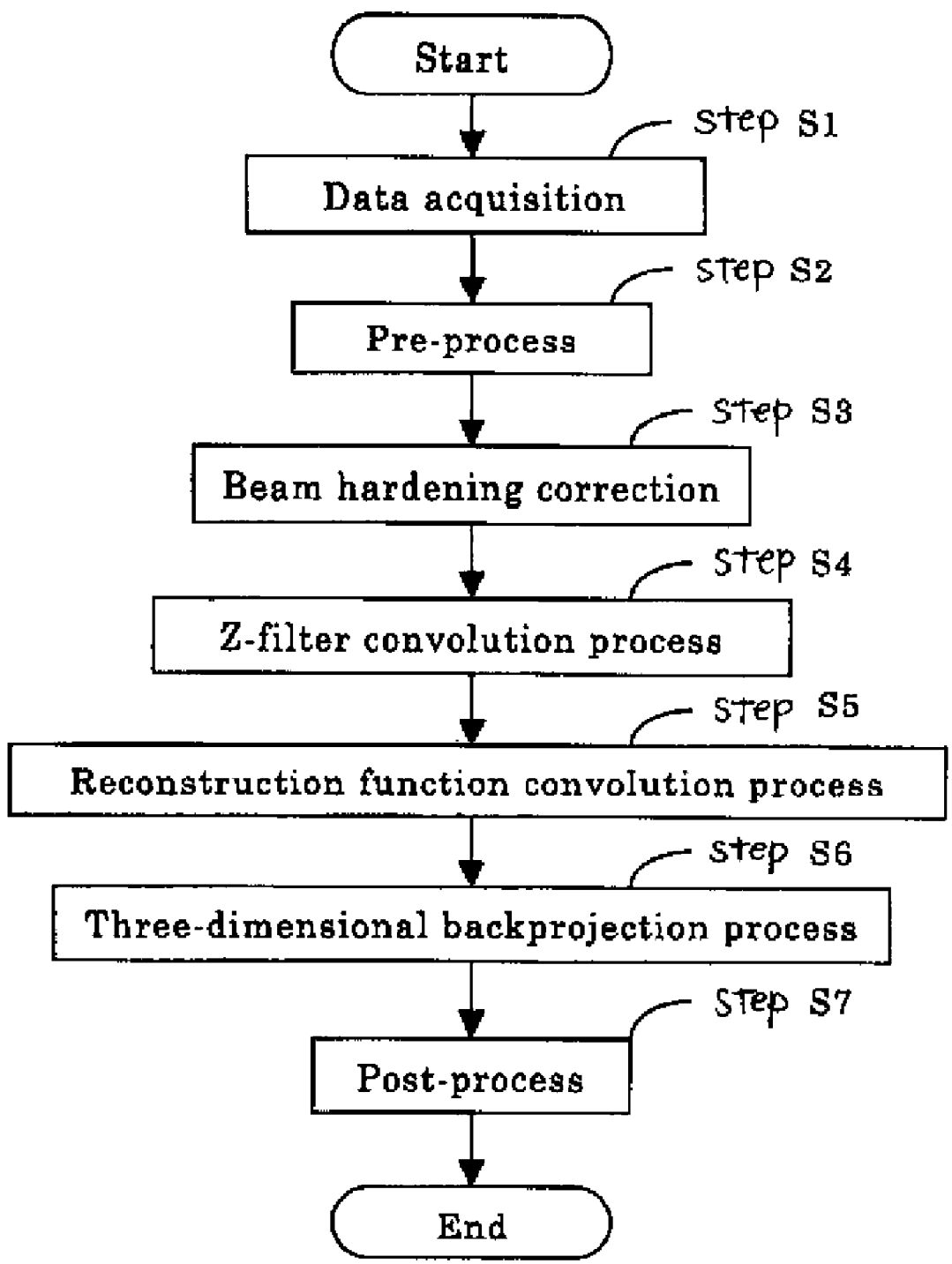
FIG. 5 is a flowchart showing a schematic operation for image reconstruction, of the X-ray CT apparatus according to the one embodiment of the present invention.

FIG. 5 is a flowchart showing rough outlines of operations for the tomographic image photography and scout image photography of the X-ray CT apparatus 100 of the present invention.

At Step S1, the operation of rotating the X-ray tube 21 and the multi-row X-ray detector 24 about the subject and effecting data acquisition of X-ray detector data while the cradle 12 placed on the imaging or photographing table 10 is being linearly moved, is performed upon a helical scan. A z-direction coordinate position Ztable(view) is added to X-ray detector data D0(view, j, i) (where j=1 to ROW, and I=1 to CH) indicated by a view angle view, a detector row number j and a channel number i thereby carrying out data acquisition relative to a range at a constant speed.

The z-direction coordinate position may be added to X-ray projection data or may be used in association with the X-ray projection data as another file. Information about the z-direction coordinate position is used where the X-ray projection data is three-dimensionally image-reconstructed upon the helical shuttle scan and the variable pitch helical scan. Using the same upon the helical scan, conventional scan (axial scan) or cine scan, an improvement in the accuracy of an image-reconstructed tomographic image and an improvement in its quality n be also realized As the z-direction coordinate position, position control data on the cradle 12 placed on the photographing table 10 may be used. Alternatively, z direction coordinate positions at respective times, which are predicted from the imaging operation set upon the imaging condition setting, may also be used.

Upon the variable helical scan or helical shuttle scan, data acquisition will be carried out even at acceleration and deceleration in addition to the data acquisition for the range at the constant speed.

Upon the conventional scan (axial scan) or the cine scan, the data acquisition system is rotated once or plural times while the cradle 12 placed on the photographing table 10 is being fixed to a given z-direction position, thereby to perform data acquisition of X-ray detector data. The cradle 12 is moved to the next z direction position as needed and thereafter the data acquisition system is rotated once or plural times again to perform data acquisition of X-ray detector data.

Upon the scout image photography, the operation of fixing the X-ray tube 21 and the multi-row X-ray detector 24 and performing data acquisition of X-ray detector data while the cradle 12 placed on the photographing table 10 is being linearly moved, is performed.

Figure 6:
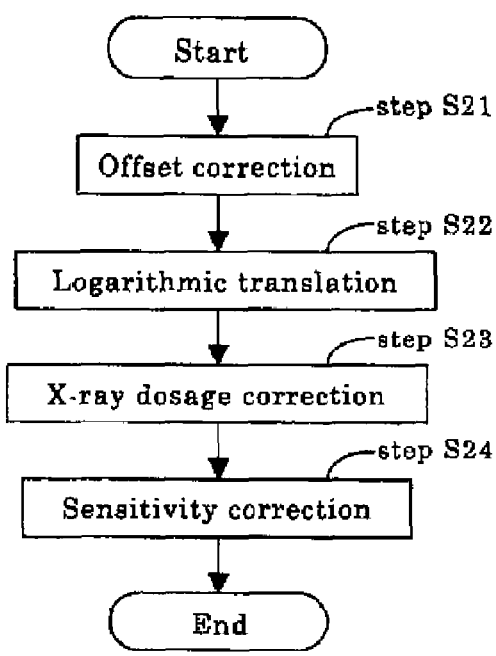
FIG. 6 is a flowchart depicting the details of a pre-process.

At Step S2, a pre-process is performed on the X-ray detector data D0(view, j, i) to convert it into projection data. FIG. 6 shows a specific process about the pre-process at Step S2. At Step S21, an offset correction is performed. At Step S22, a logarithmic translation is performed. At Step S23, an X-ray dosage correction is performed. At Step S24, a sensitivity correction is performed.

In the case of the scout image photography, the pre-processed X-ray detector data is completed as a scout image if a pixel size as viewed in the channel direction and a pixel size as viewed in the z direction corresponding to the linear traveling direction of the cradle 12 are displayed in match with the display pixel size of the monitor 6.

Referring back to FIG. 5, a beam hardening correction is effected on the pre-processed projection data D1(view, j, i) at Step S3. Assuming that upon the beam hardening correction at Step S3, projection data subjected to the sensitivity correction of Step S24 of the pre-process S2 is defined as D1(view, j, i) and data subsequent to the beam hardening correction of Step S3 is defined as D11(view, j, i), the beam hardening correction of Step S3 is expressed in the form of, for example, a polynomial as shown below (Equation 1). Incidentally, a multiplication operation or computation is expressed in "•" in the present embodiment.

[Equation 1]

$$D11(view,j,i)=D1(view,j,i) \cdot (Bo(j,i)+B_1(j,i) \cdot D1(view,j,i)+B_2(j,i) \cdot D1(view,j,i)^2) \quad (1)$$

Since, at this time, beam hardening corrections independent of one another every j row of detector can be performed, the differences in X-ray energy characteristics of the detectors for every row can be costed respective tube voltages of the data acquisition system are different on the imaging conditions.

At Step S4, a z-filter convolution process for applying filters in the z direction (row direction) is effected on the projection data D11(view, j, i) subjected to the beam hardening correction.

That is, projection data of the multi-row X-ray detector D11(view, j, i) (where i=1 to CH and j=1 to ROW) subjected to the pre-process at the data acquisition system and to the beam hardening correction at each view angle, is subjected to filters in which, for example, such row-direction filter sizes as expressed in the following equations (Equation 2) and (Equation 3) are five rows, in the row direction.

[Equation 2]

$$(w_1(i), w_2(i), w_3(i), w_4(i), w_5(i)) \quad (2)$$

where the sum of the above equation (2) is as follows:

[Equation 3]

$$\sum_{k=1}^{5} w_k(i) = 1 \quad (3)$$

This will be defined as the sum of all wk(i), from k equals one to infinity.

The corrected detector data D12(view, j, i) is expressed as follows (given by the following equation 4):

[Equation 4]

$$D12(\text{view}, j, i) = \sum_{k=1}^{5} (D11(\text{view}, j+k-3, j) \cdot w_k(j)) \quad (4)$$

Incidentally, assuming that the maximum value of the channel is CH and the maximum value of the row is ROW, the following equations (Equations 5 and 6) are established.

[Equation 5]

$$D11(\text{view},-1,i) = D11(\text{view},0,i) = D11(\text{view},1,i) \quad (5)$$

[Equation 6]

$$D11(\text{view},\text{ROW},i) = D11(\text{view},\text{ROW}+1,i) = D11(\text{view},\text{ROW}+2,i) \quad (6)$$

When row-direction filter coefficients are changed for every channel, slice thicknesses can be controlled depending upon the distance from an image reconstruction center. In a tomographic image, its peripheral portion generally becomes thick in slice thickness than the reconstruction center thereof. Therefore, the row-direction filter coefficients are changed at the central and peripheral portions so that the slice thicknesses can also be made uniform even at the peripheral portion and the image reconstruction center. When, for example, the row-direction filter coefficients are changed at the central and peripheral portions, the row-direction filter coefficients are changed extensively in width in the neighborhood of a central channel, and the row-direction filter coefficients are changed narrowly in width in the neighborhood of a peripheral channel, each slice thickness can be made approximately uniform even at the peripheral portion and image reconstruction central portion.

By controlling the row direction filter coefficients for the central and peripheral channels of the multi-row X-ray detector 24 in this way, each slice thickness can also be controlled at the central and peripheral portions. Slightly thickening the slice thickness by the row-direction filters provides a great improvement in both artifact and noise. Thus, the degree of an improvement in artifact and the degree of an improvement in noise can also be controlled. That is, the three-dimensionally image-reconstructed tomographic image, i.e., the image quality in the xy plane can be controlled. As another embodiment, a tomographic image having a thin slice thickness can also be realized by subjecting the row-direction (z-direction) filter coefficients to deconvolution filters.

At Step S5, a reconstruction function convolution process is performed. That is, projection data is subjected to Fourier transformation for performing transformation into a frequency domain or region and multiplied by a reconstruction function, followed by being subjected to inverse Fourier transformation. Assuming that upon the reconstruction function convolution process S5, projection data subsequent to the z filter convolution process is defined as D12, projection data subsequent to the reconstruction function convolution process is defined as D13, and the convoluting reconstruction function is defined as Kernel(j), the reconstruction function convolution process is expressed as follows (Equation 7). Incidentally, a convolution computation or operation is expressed in "*" in the present embodiment.

[Equation 7]

$$D13(\text{view},j,i) = D12(\text{view},j,i) * \text{Kernel}(j) \quad (7)$$

That is, since the reconstruction function kernel (j) can perform reconstruction function convolution processes independent of one another for every j row of detector, the difference between noise characteristics set for every row and the difference between resolution characteristics can be corrected.

At Step S6, a three-dimensional backprojection process is effected on the projection data D13(view, j, i) subjected to the reconstruction function convolution process to determine backprojection data D3(x, y, z). An image to be image-reconstructed is three dimensionally image-reconstructed on a plane, i.e., an xy plane orthogonal to the z axis. A reconstruction area or plane P to be shown below is assumed to be parallel to the xy plane. The three-dimensional backprojection process will be explained later referring to FIG. 5.

At Step S7, a post-process including image filter convolution, CT value conversion and the like is effected on the backprojection data D3(x, y, z) to obtain a tomographic image D31(x, y, z).

Assuming that upon the image filter convolution pre in the post-process, a tomographic image subsequent to the three-dimensional backprojection is defined as D31(x, y, z), data subsequent to the image filter convolution is defined as D32 (x, y, z), and a two-dimensional image filter subjected to convolution on the xy plane corresponding to a tomographic image plane is defined as Filter(z), the following equation (Equation 8) is established.

[Equation 8]

$$D32(x,y,z) = D31(x,y,z) * \text{Filter}(z) \quad (8)$$

That is, since the image filter convolution processes independent of one another for every tomographic image at each z-coordinate position can be carried out, the differences between noise characteristics and between resolution characteristics for every row can be corrected.

An image space z-direction filter convolution process shown below may be carried out after the two-dimensional image filter convolution process. This image space z-direction filter convolution process may be performed before the two-dimensional image filter convolution process. Further, a three-dimensional image filter convolution process may be performed to produce such an effect as to share both of the two-dimensional image filter convolution process and the image space z direction filter convolution process.

Assuming that upon the image space z-direction filter convolution process, a tomographic image subjected to the image space z-direction filter convolution process is defined as D33 (x, y, z) and a tomographic image subjected to the two-dimensional image filter convolution process is defined as D32(x, y, z), the following equation (Equation 9) is established as follows. However, at an image space z-direction filter coefficient at which a z-direction width is 2l+1, v(i) is expressed in the form of such a coefficient row as shown below (Equation 10).

[Equation 9]

$$D33(x, y, z) = \sum_{i=-l}^{l} D32(x, y, z+i) \cdot v(i) \quad (9)$$

[Equation 10]

$$v(-l), v(-l+1), \ldots v(-l), v(0), v(l-1), v(l) \quad (10)$$

Upon the helical scan, the image space filter coefficient v(i) may be an image space z-direction filter coefficient independent upon the z-direction position. However, when the conventional scan (axial scan) or cine scan is performed using the two-dimensional X-ray area detector 24 or multi-row X-ray detector 24 or the like broad in detector width in the z-direction in particular, the image space z-direction filter coefficient v(i) may preferably use an image space z-direction filter coefficient that depends upon the position of each X-ray detector row in the z direction. This is because it is further effective since detailed adjustments dependent on the row position of each tomographic image can be made.

The resultant tomographic image is displayed on the monitor 6.

(Flowchart for Three-Dimensional Backprojection Process)

Figure 7:
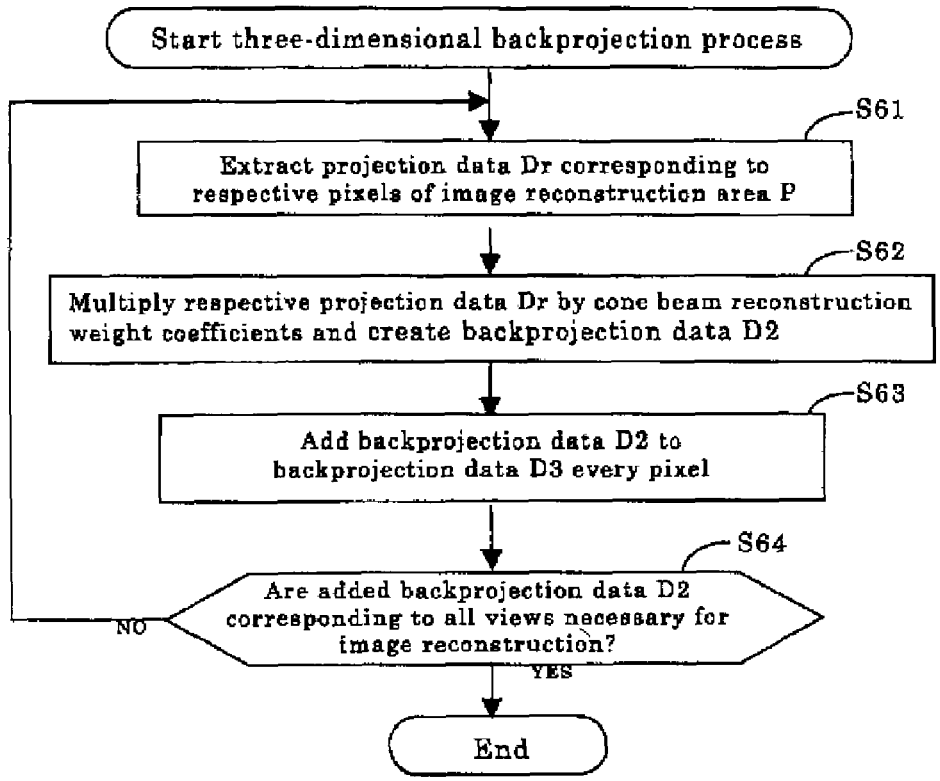
FIG. 7 is a flowchart illustrating the details of a three-dimensional image reconstructing process.

FIG. 7 shows the details of Step S6 in FIG. 5 and is a flowchart showing the three-dimensional backprojection process.

In the present embodiment, an image to be image-reconstructed is three-dimensionally image-reconstructed on a plane, i.e., an xy plane orthogonal to the z axis. The following reconstruction area P is assumed to be parallel to the xy plane.

At Step S61, attention is paid to one of all views (i.e., views corresponding to 360° or views corresponding to "180°+fan angles") necessary for image reconstruction of each tomographic image. Projection data Dr corresponding to respective pixels in the reconstruction area P are extracted.

Figure 8:
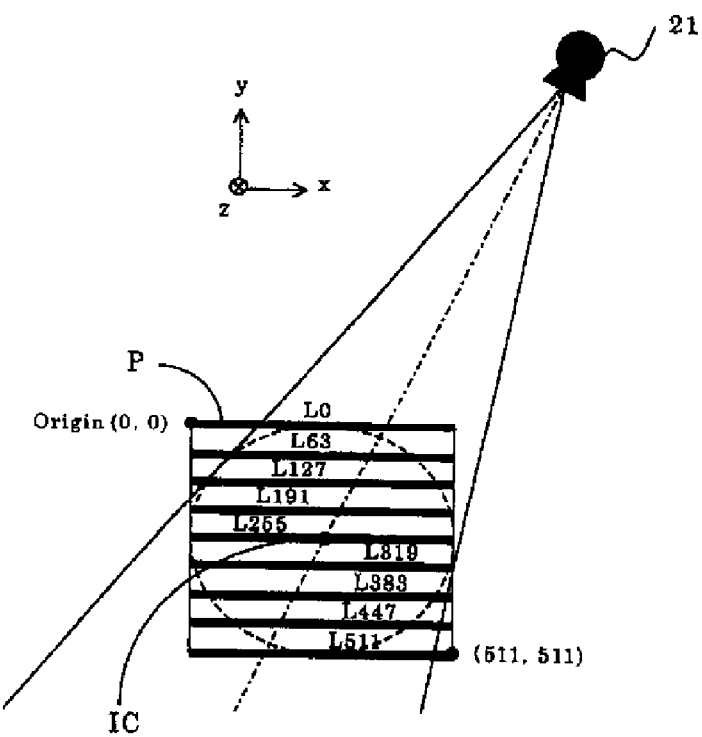
FIG. 8 is a conceptual diagram showing a state in which lines on an image reconstruction area are projected in an X-ray penetration direction.
Figure 8:
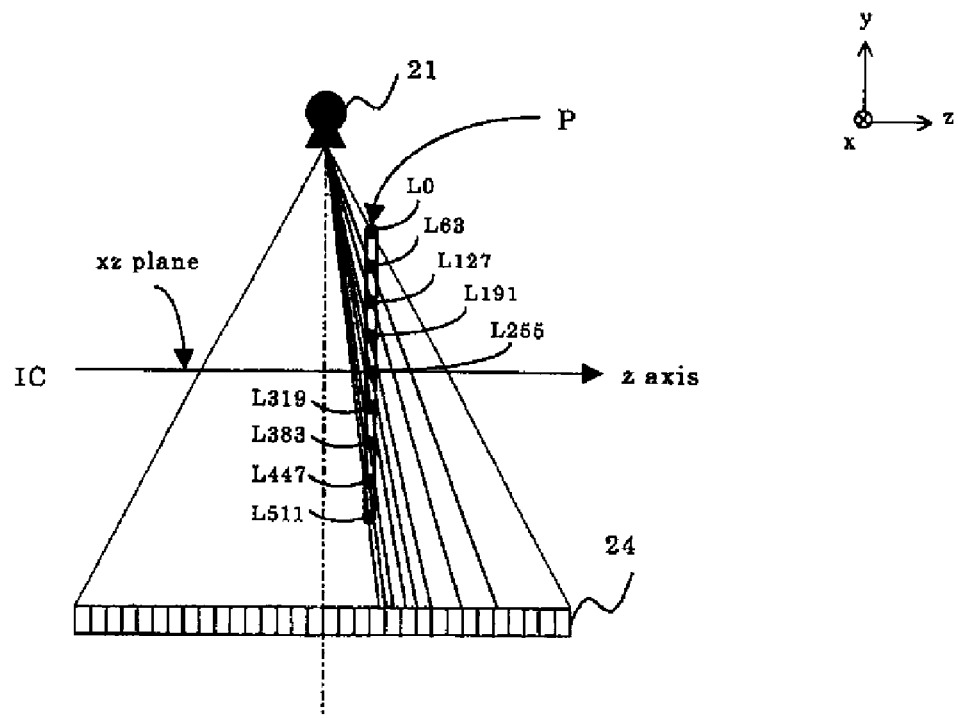
Figure 9:
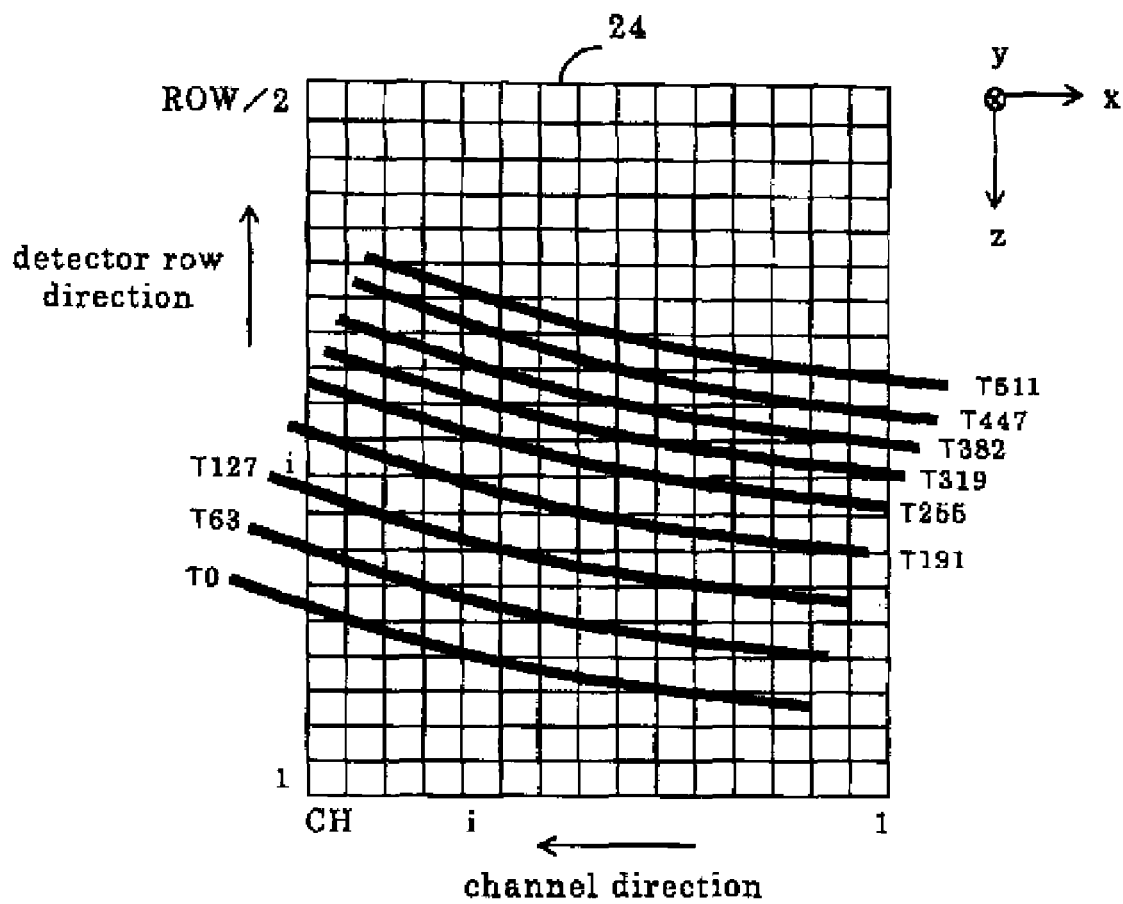
FIG. 9 is a conceptual diagram illustrating lines projected onto an X-ray detector plane.

The projection data Dr will now be explained using FIGS. 8(a) and 8(b) through FIG. 10. FIGS. 8(a) and 8(b) are conceptual diagrams showing the projection of lines on a reconstruction area in an X-ray penetration direction, wherein FIG. 8(a) shows an xy plan and FIG. 8(b) shows a yz plane. FIG. 9 is a conceptual diagram showing the respective lines in an image reconstruction plane, which are projected onto an X-ray detector plane.

As shown in FIGS. 8(a) and 8(b), a square area of 512×512 pixels, which is parallel to the xy plane, is assumed to be a reconstruction area P. A pixel row L0 parallel to the x axis of y=0, a pixel row L63 of y=63, a pixel row L127 of y=127, a pixel row L191 of y=191, a pixel row L255 of y=255, a pixel row L319 of y=319, a pixel row L383 of y=383, a pixel row L447 of y=447, and a pixel row L511 of y=511 are taken as rows. If projection data on lines T0 through T511 shown in FIG. 9 obtained by projecting the pixel rows L0 through L511 onto the plane of the multi-row X-ray detector 24 in an X-ray penetration direction are extracted, then they result in projection data Dr(view, x, y) of the pixel lows L0 through L511. However, x and y correspond to the respective pixels (x, y) of the tomographic image.

The X-ray penetration direction is determined depending on geometrical positions of the X-ray focal point of the X-ray tube 21, the respective pixels and the multi-row X-ray detector 24. Since, however, the z coordinates z(view) of X-ray detector data D0(view, j, i) are known with being added to the X-ray detector data as a table linear movement z-direction position Ztable(view), the X-ray penetration direction can be accurately determined within the X-ray focal point and the data acquisition geometrical system of the multi-row X-ray detector even in the case of the X-ray detector data D0(view, j, i) placed under acceleration and deceleration.

Incidentally, when some of lines are placed out of the multi-row X-ray detector 24 as viewed in the channel direction as in the case of, for example, the line T0 obtained by projecting the pixel row L0 on the plane of the multi-row X-ray detector 24 in the X-ray penetration direction, the corresponding projection data Dr(view, x, y) is set to "0". When it is placed outside the multi-row X-ray detector 24 as viewed in the z direction, the corresponding projection data Dr(view, x, y) is determined as extrapolation.

Figure 10:
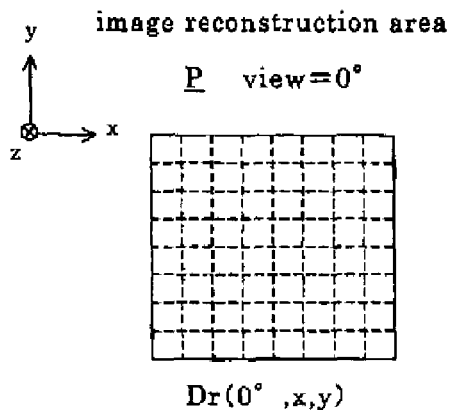
FIG. 10 is a conceptual diagram showing a state in which projection data Dr (view, x, y) is projected onto an image reconstruction area.

Thus, the projection data Dr(view, x, y) corresponding to the respective pixels of the reconstruction area P can be extracted as shown in FIG. 10.

Figure 11:
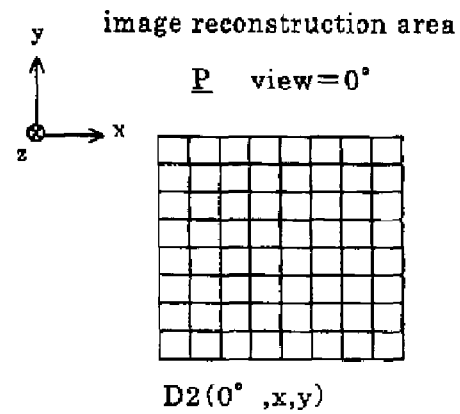
FIG. 11 is a conceptual diagram illustrating backprojection pixel data D2 of respective pixels on an image reconstruction area.

Referring back to FIG. 7, at Step S62, the projection data Dr(view, x, y) are multiplied by a cone beam reconstruction weight coefficient to create projection data D2(view, x, y) as shown in FIG. 11.

Now, the cone beam reconstruction weight coefficient w(i, j) is as follows. Generally, when the angle which a linear line connecting the focal point of the X-ray tube 21 and a pixel g(x, y) on the reconstruction area P (xy plane) at view=βa forms with a center axis Bc of an X-ray beam is assumed to be γ and its opposite view is assumed to be view=βb in the case of fan beam image reconstruction, the following equation is established.

[Equation 11]

$$\beta b = \beta a + 180° - 2\gamma \tag{11}$$

When the angles which the X-ray beam passing through the pixel g(x, y) on the reconstruction area P and its opposite X-ray beam form with the reconstruction plane P, are assumed to be αa and αb, they are multiplied by cone beam reconstruction weight coefficients ωa and ωb dependant on these and added together to determine backprojection pixel data D2(0, x, y) in the following manner.

[Equation 12]

$$D2(0,x,y) = (\omega a \cdot D2(0,x,y)\_a + \omega b \cdot D2(0,x,y)\_b \tag{12}$$

where D2(0,x,y)_a indicates backprojection data for the view βa, and D2(0,x,y)_b indicates backprojection data for the view βb.

Incidentally, the sum of the cone beam reconstruction weight coefficients corresponding to the beams opposite to each other is as follows:

[Equation 13]

$$\omega a + \omega b = 1 \tag{13}$$

The above addition with multiplication of the cone beam reconstruction weight coefficients ωa and ωb enables a reduction in cone angle artifacts For instance, the cone beam reconstruction weight coefficients ωa and ωb can make use of ones obtained by the following equations. Incidentally, ga indicates a weight coefficient of the view βa, and gb indicates a weight coefficient of the view βb, respectively.

Assuming that ½ of a fan beam angle is γmax, the following equations (Equation 14 to Equation 19) are established.

[Equation 14]

$$ga = f(\gamma max, \alpha a, \beta a) \tag{14}$$

[Equation 15]

$$gb = f(\gamma max, \alpha b, \beta b) \tag{15}$$

[Equation 16]

$$xa = 2 \cdot ga^q / (ga^q + gb^q) \tag{16}$$

[Equation 17]

$$xb = 2 \cdot gb^q / (ga^q + gb^q) \tag{17}$$

[Equation 18]

$$wa = xa^2 \cdot (3 - 2xa) \quad (18)$$

[Equation 19]

$$wb = xb^2 \cdot (3 - 2xb) \quad (19)$$

(For instance, q=1)

Assuming that as examples of ga and gb, max[ ] are defined as functions that take large values, the following equations (Equation 20 and Equation 21) are given as follows:

[Equation 20]

$$ga = \max[0, \{(\pi/2 + \gamma\max) - |\beta a|\}] \cdot |\tan(\alpha a)| \quad (20)$$

[Equation 21]

$$gb = \max[0, \{(\pi/2 + \gamma\max) - |\beta b|\}] \cdot \tan(\alpha b)| \quad (21)$$

In the case of the fan beam image reconstruction each pixel on the reconstruction area P is for multiplied by a distance coefficient. Assuming that the distance from the focal point of the X-ray tube 21 to each of the detector row j and channel i of the multi-row X-ray detector 24 corresponding to the projection data Dr is r0, and the distance from the focal point of the X-ray tube 21 to each pixel on the reconstruction area P corresponding to the projection data Dr is r1, the distance coefficient is given as (r1/f0)2.

Figure 12:
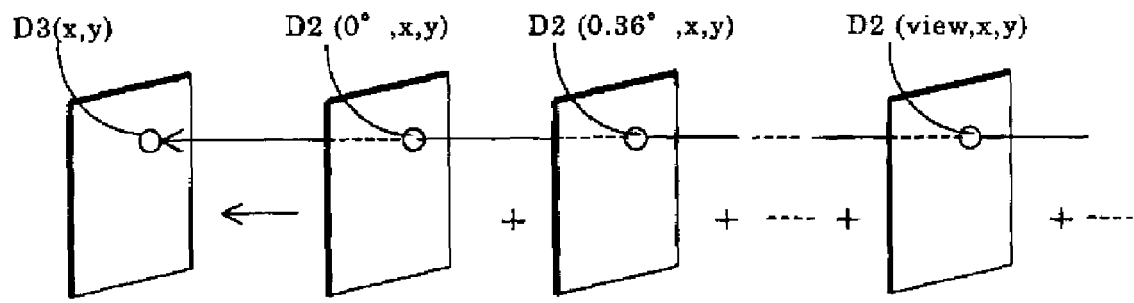
FIG. 12 is an explanatory diagram depicting a state in which backprojection pixel data D2 are added together over all views in association with pixels to obtain backprojection data D3.

In the case of parallel beam image reconstruction, each pixel on the reconstruction area P may be multiplied by the cone beam reconstruction weight coefficient w(i, j) alone, At Step S63, the projection data D2(view, x, y) is added to its corresponding backprojection data D3(x, y) cleared in advance in association with each pixel. FIG. 12 shows the concept that the projection data D2(view, x, y) is added for every pixel At Step S64, Steps S61 through S63 are repeated with resect to all views (i.e., views corresponding to 360° or views corresponding to "180°+fan angles") necessary for image reconstruction of each tomographic image. Adding all the views necessary for the image reconstruction makes it possible to obtain backprojection data D3(x, y) shown in the left drawing of FIG. 12.

Figure 13:
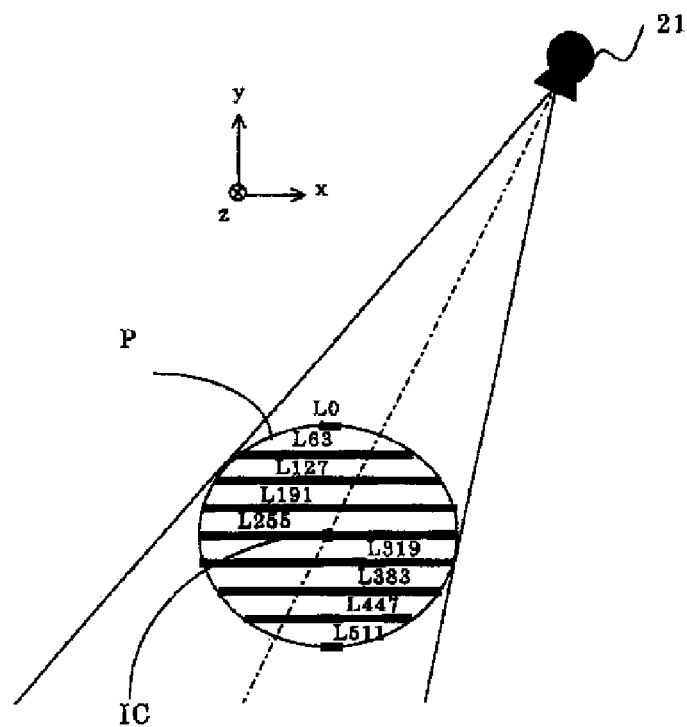
FIG. 13 is a conceptual diagram showing a state in which lines on a circular image reconstruction area are projected in an X-ray penetration direction.
Figure 13:
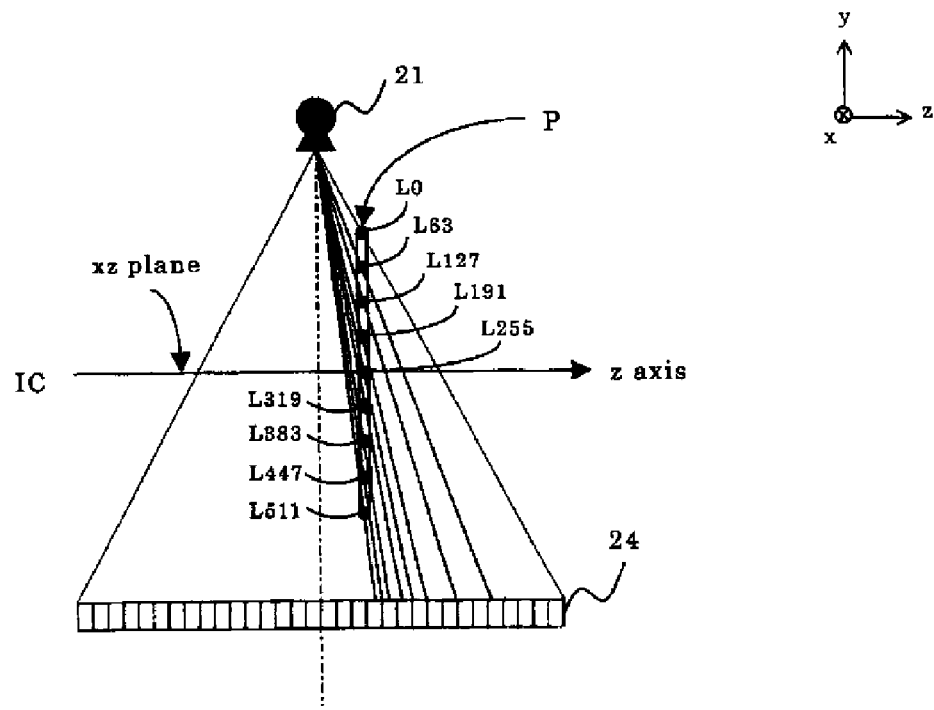

The flowchart for the three-dimensional backprojection process of FIG. 7 is equivalent to one in which the image reconstruction area P shown in FIG. 8 is described as a square of 512×512 pixels. However, no limitation is imposed on it. FIGS. 13(*a*) and 13(*b*) are respectively conceptual diagrams each showing a state in which lines on a circular image reconstruction area are projected in an X-ray penetration direction, wherein FIG. 13(*a*) shows an xy plane, and FIG. 13(*b*) shows a yz plane.

As shown in FIGS. 13(*a*) and 13(*b*), the reconstruction area P may be set as a circular area whose diameter is 512 pixels, without setting it as the square area of 512×512 pixels.

An embodiment illustrative of a heart imaging method capable of performing imaging with good quality at a high speed under low exposure using the X-ray CT apparatus is shown below.

A first embodiment shows an embodiment wherein the appropriateness of the phase of an electrocardiographic signal is determined in advance by a high-speed helical scan large in helical pitch at low X-ray dosage and thereafter a helical scan for an actual scan is performed by means of test injection or contrast agent synchronous photography.

A second embodiment shows an embodiment related to a method of contrast agent synchronous photography or imaging.

First Embodiment

The first embodiment illustrates the embodiment wherein the appropriateness of the phase of the electrocardiographic signal is determined in advance by the high-speed helical scan large in helical pitch at low X-ray dosage and thereafter the helical scan for the actual scan is performed by means of test injection or contrast agent synchronous photography.

FIGS. 16, 17, 18 and 19 are respectively diagrams for describing the prior art and respectively show the image of the conventional heart imaging process. So-called electrocardiographic synchronous photography or imaging synchronized with the heartbeat has heretofore been performed upon photography of a cardiac coronary r or the like. As the electrocardiographic synchronous photography or imaging, there are known prospective imaging in which while the average of a plurality of immediately-preceding cardiac cycles or periods is being observed, projection data are acquired in sync with, for example, 75% phase of the average cardiac period considered to be a cardiac phase stablest in heart, thereby performing image reconstruction, and so-called retrospective imaging in which an electrocardiographic signal and X-ray projection data are stored in association with each other in advance, and the X-ray projection data of the cardiac phase at image reconstruction is extend, thereby performing image reconstruction. Since there is a case in which upon the prospective imaging, scan control does not work well due to arrhythmias, the retrospective imaging is in the mainstream.

Figure 22:
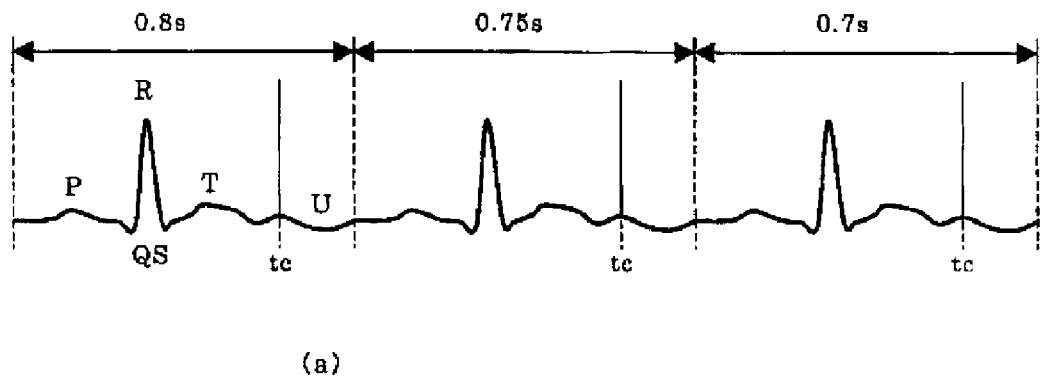
FIG. 22(a) is a diagram showing the waveform of an electrocardiographic signal of a subject.
FIG. 22(b) is a diagram illustrating a sync signal based on a cardiac phase.
FIG. 22(c) is a diagram depicting a sync signal based on a cardiac triggered phase.
Figure 22:
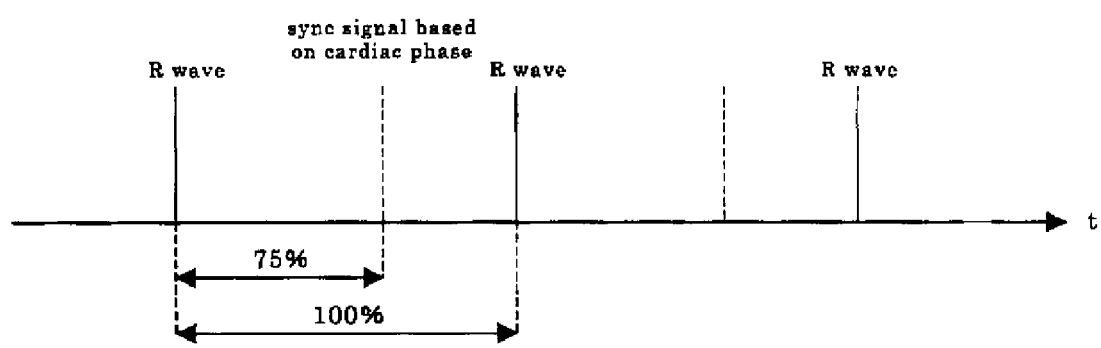
Figure 22:
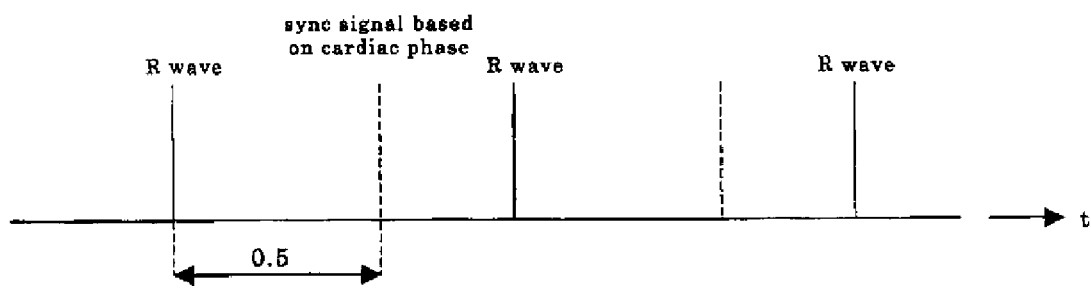

FIG. 22(*a*) shows a general electrocardiographic signal. Assuming now that the heart rate is 75 bmp (beat per minute), a cardiac period becomes 0.8 seconds and such electrocardiographic waveforms (P wave, QRS wave, T wave and U wave) as shown in the drawing appear in this period. At the timing of the P wave, the cardiac atria is excited and shrunk so that blood flows from a large vein and a pulmonary vein flow into the cardiac ventricle or chamber. At the timing of the QRS wave following the above timing, the cardiac atria simmers down or falls out of excitation and the cardiac ventricle or chamber is excited and shrunk, thereby squeezing the blood flow of the cardiac chamber into a main artery and a pulmonary a At the timing of the subsequent T wave, the cardiac chamber simmers down. And the motion of the heart becomes most gradual at the timing (cardiac phase 75%) of the subsequent U wave.

As the method of image-reconstructing a tomographic image such as the cardiac coronary artery or the like, there has heretofore been known a so-called multi-segment image reconstructing method. In the present method, projection data about the cardiac phase 75% are extracted based on the electrocardiographic signal detected simultaneously with the cardiac helical scan, and the extracted segment data are combined by view angles necessary for the image reconstruction of one slice, whereby the corresponding tomographic image can be image-reconstruct.

In general, there is a need to set projection data corresponding to at least fan angles+180° as view angles for the purpose of the image reconstruction corresponding to one slice. When it is however not possible that X-ray projection data corresponding to one rotation of the gantry covers such a projection data, segment data extracted from a cardiac period or heartbeat range of continuous two heartbeats or more are combined, thereby image-reconstructing a tomographic image corresponding to one slice.

In recent years, X-ray detectors have been multirowed and the width of each X-ray detector has been increased, and the rotational speed of the gantry has been also speeded up. However, the present situation is that since the z-direction width of the X-ray detector is not sufficiently broad and the imaging of the whole heart cannot be attained by only one scan upon the conventional scan (axial scan) or cine scan, X-ray projection data corresponding to plural segments are combined by the cardiac helical scan to perform image reconstruction.

Figure 21:
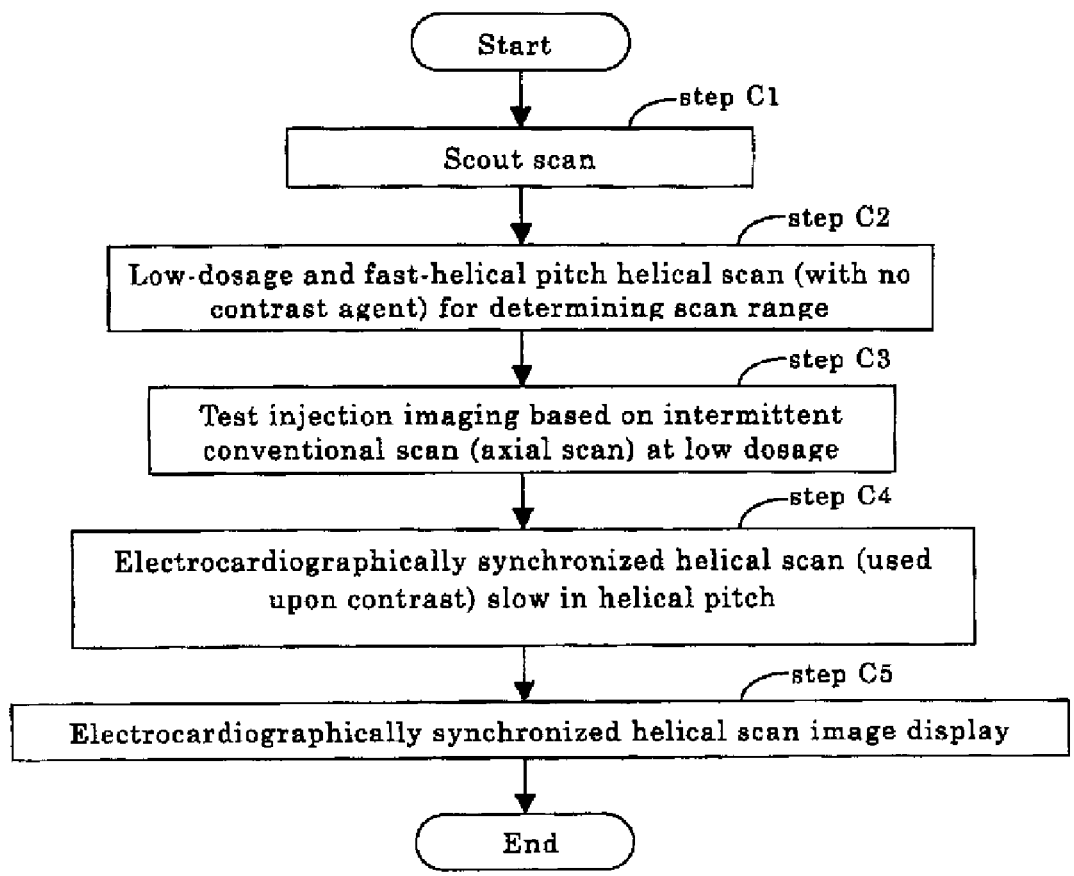
FIG. 21 is a flowchart illustrating conventional cardiac photography

The flow of the conventional heart imaging method is shown in FIG. 21.

At Step C1, a scout scan is performed.

At Step C2, a low-dosage and fast-helical pitch helical scan (with no contrast agent) for determining a scan range is performed.

At Step C3, test injection imaging or photography by an intermittent conventional scan (axial scan) at a low dosage is carried out.

At Step C4, an electrocardiographically synchronized helical scan (used upon contrast) slow in helical pitch is performed.

At Step C5, an electrocardiographically synchronized helical scan image display is performed.

The cardiac imaging has heretofore bee carried out in this way.

However, the helical scan slow in helical pitch, which is carried out at Step C4, is slow 0.2 or so in helical pitch, and the dose of X-rays radiated to the subject was greater than at the normal scan.

Figure 16:
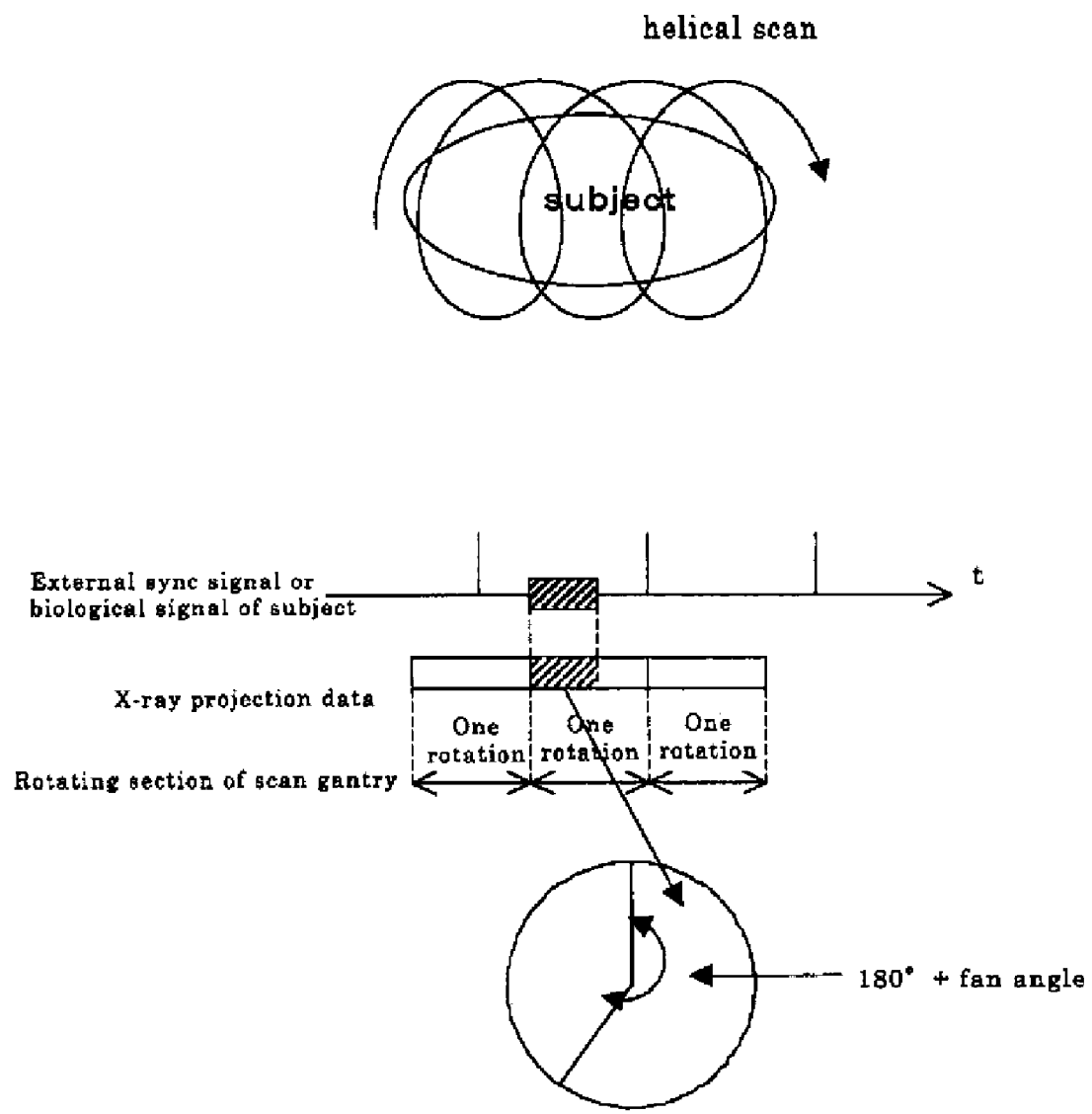
FIG. 16 is an explanatory diagram showing helical scan half scan (180°+fan angle) image reconstruction of one segment synchronized with a biological signal.
Figure 17:
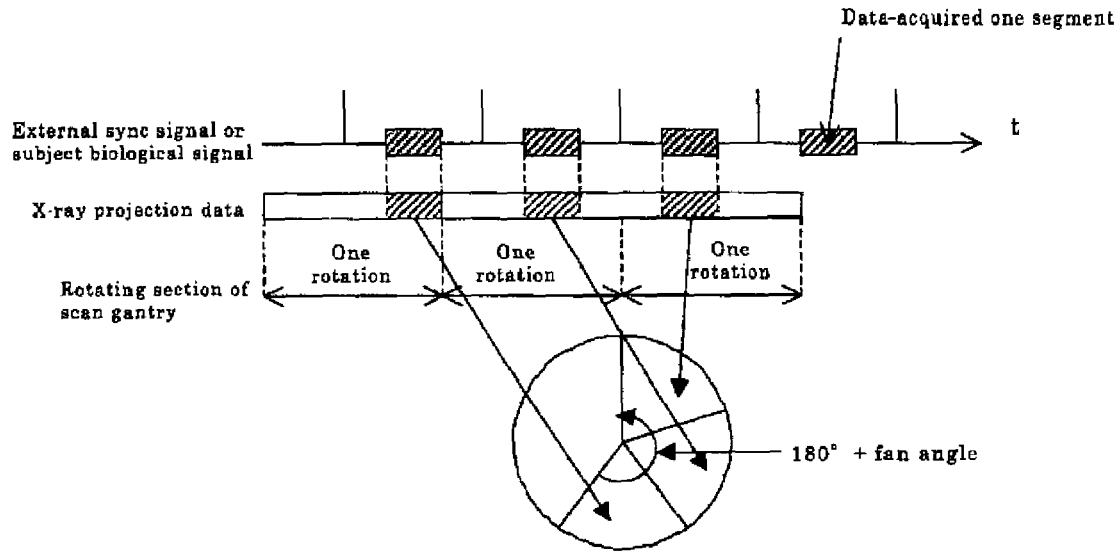
FIG. 17 is an explanatory diagram illustrating helical half scan (180°+fan angles) image reconstruction divided into three segments.
Figure 18:
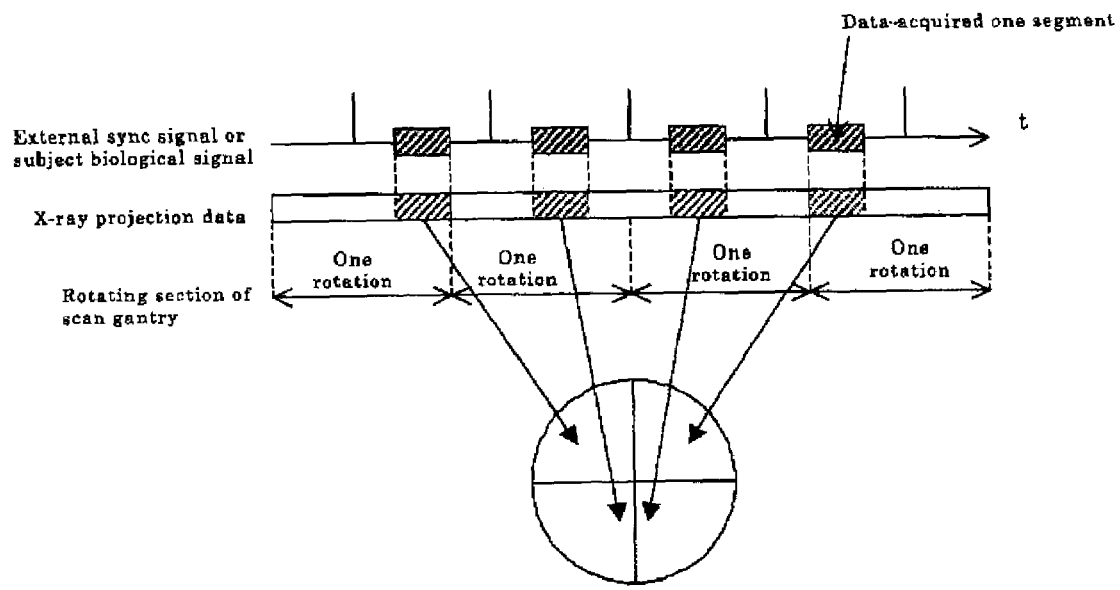
FIG. 18 is an explanatory diagram depicting helical full scan (360°) image reconstruction divided into four segments.

Upon the cardiac helical scan at Step C4, such X-ray data acquisition and its image reconstruction as shown in FIGS. 16, 17 and 18 have been carried out. In such cases as shown in FIGS. 17 and 18 in particular, the X-ray projection data corresponding to the fan angles +180° or 360° are divided to carry out the image reconstruction. Therefore, each joining portion of the X-ray projection data is not connected smoothly, thereby leading to the occurrence of artifacts.

Figure 19:
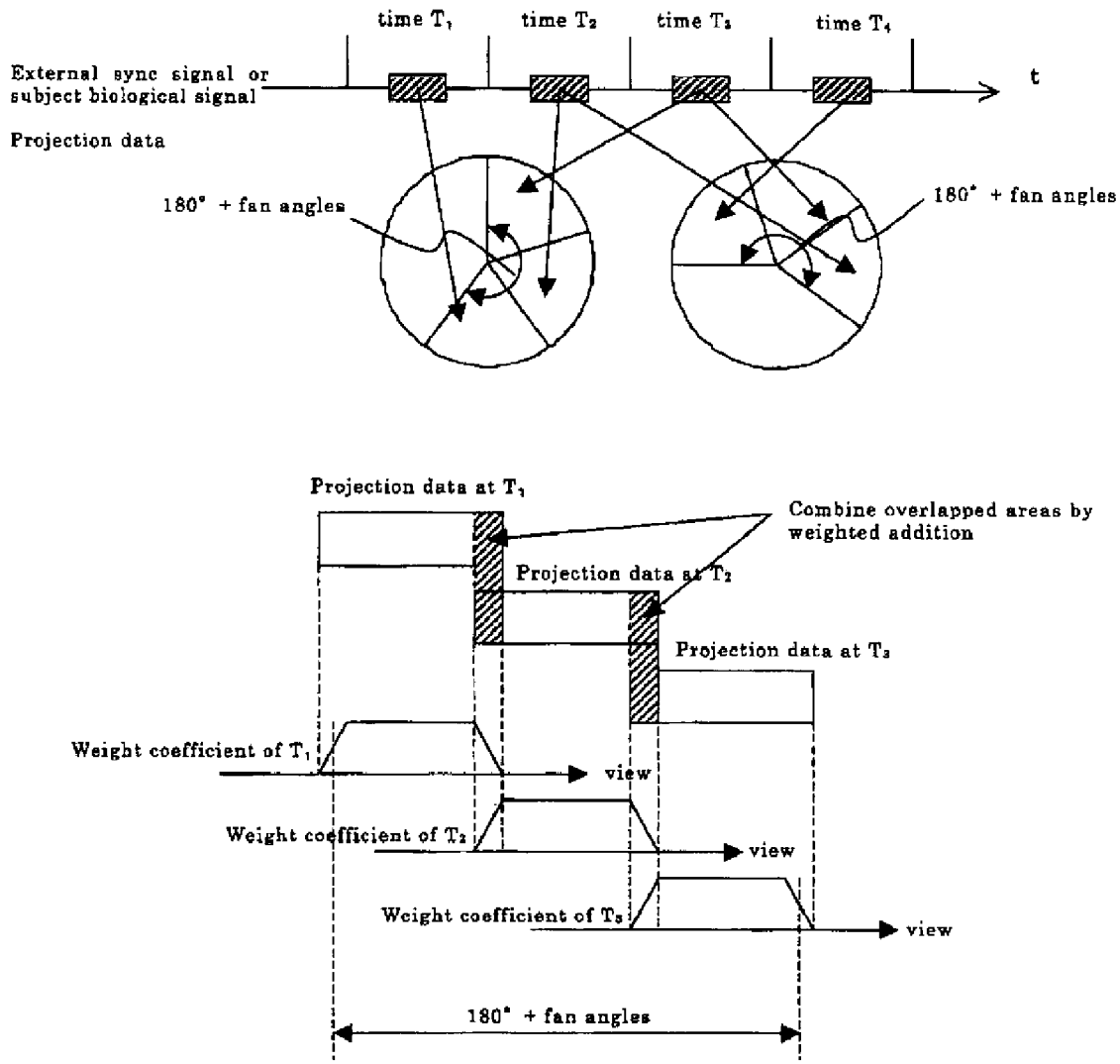
FIG. 19 is a diagram showing weighted addition of projection data on respective segments.
Figure 20:
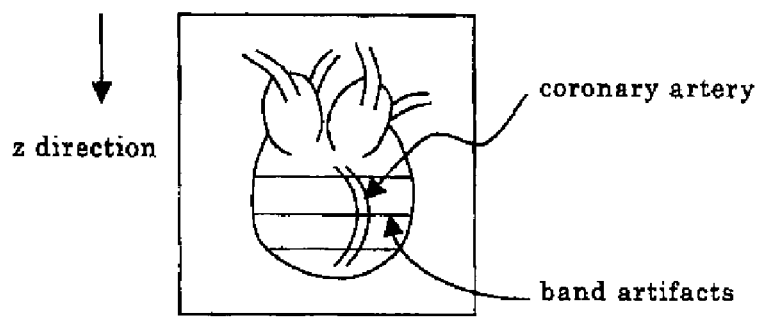
FIG. 20 is a diagram illustrating band artifacts at a cardiac three-dimensional display.

In FIG. 19, the joining portions of the X-ray projection data are caused to overlap each other in such a manner that the joining portions thereof become preferably smooth. The X-ray projection data on both side of the joining portion is multiplied by a weight coefficient to make weighted addition, thereby combining the X-ray projection data. Since, however, the X-ray projection data different in time and cardiac period or heartbeat are combined, the discontinuity in joining portion cannot be resolved even this unless reproducibility of body motion of the subject is obtained, so artifacts on the tomographic image and banding artifacts at the three-dimensional image display cannot be avoided.

In the present embodiment, the following points are taken into consideration and improved as important points.
(1) Data acquisition is performed by a one helical scan continuous in a time direction as a countermeasure for the absence of the reproducibility of the subject's body motion.
(2) Three-dimensional image reconstruction is used in which artifacts are less reduced even though a high-speed helical scan large in helical pitch is performed.
(3) The conventional cardiac imaging method is usable when the cardiac period is short.

Figure 23:
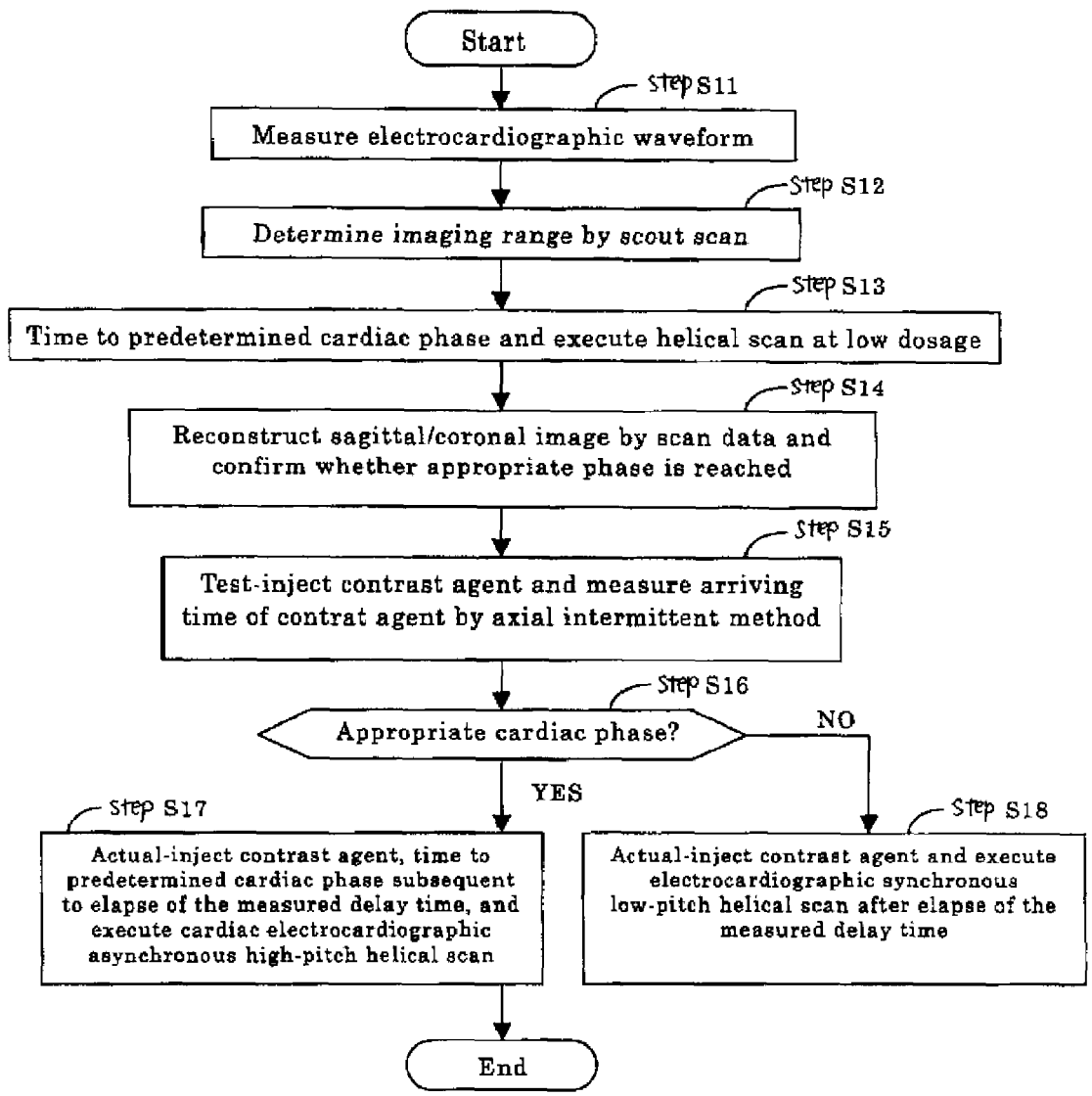
FIG. 23 is a flowchart of a first embodiment.

FIG. 23 shows a flowchart for describing cardiac photography or imaging in the first embodiment. The cardiac imaging of the first embodiment will be explained with reference to the figure.

Incidentally, a scan width of one example, a gantry rotational speed, and a helical pitch for a high-pitch helical scan are assumed to be 40 mm, 0.35 seconds per rotation and 1.375 respectively in the following description. Here, the helical pitch indicates a ratio S/D between a z-direction width D of an X-ray beam and the amount S of subject's motion per rotation of an X-ray data acquisition system.

At Step S11 in FIG. 23, the electrocardiograph 31 is mounted to the subject to acquire or collect an electrocardiographic signal.

At Step S12, an imaging range is designated by a scout image obtained by a scout scan for the subject, and a cardiac area of the scout image is designated. The resultant scout image is displayed on the display screen R of FIG. 14, and a cardiac position is designated. Further, an operator sets a scan range for a subsequent helical scan and an image reconstruction range. The helical scan of one example st at a body-axis direction z position zs of the subject and ends at ze.

Referring back to FIG. 23, at Step S13, a low dosage-based high-speed helical scan large in helical pitch is performed at such a timing that, for example, a cardiac phase of 75±5% of a cardiac period P or a cardiac phase of a cardiac period P+0.5 seconds is placed in a z-direction central position of an imaging range for the helical scan as a predetermined cardiac phase while electrocardiographic waveforms are being observed.

Incidentally, the helical scan at Step S13 and the image reconstruction at Step S14 subsequent to Step S13 intend to photograph or image portions or regions clearly undisplayed at the scout photography at a low dosage, perform image reconstruction at high speed, and confirm the condition for imaging or photographing a cardiac portion or region. They are not necessarily essential.

The helical scan at Step S13 may preferably be performed using a high-speed helical scan large in helical pitch and its method to be performed at Step S17 to be described later. This is not necessarily required so. At least, the helical scan at Step 13 will be performed to confirm whether the present apparatus detects a proper cardiac phase and photograph or image a proper phase corresponding to the cardiac phase, by using the low-dosage scan at Step S13 and the image reconstruction.

Figure 24:
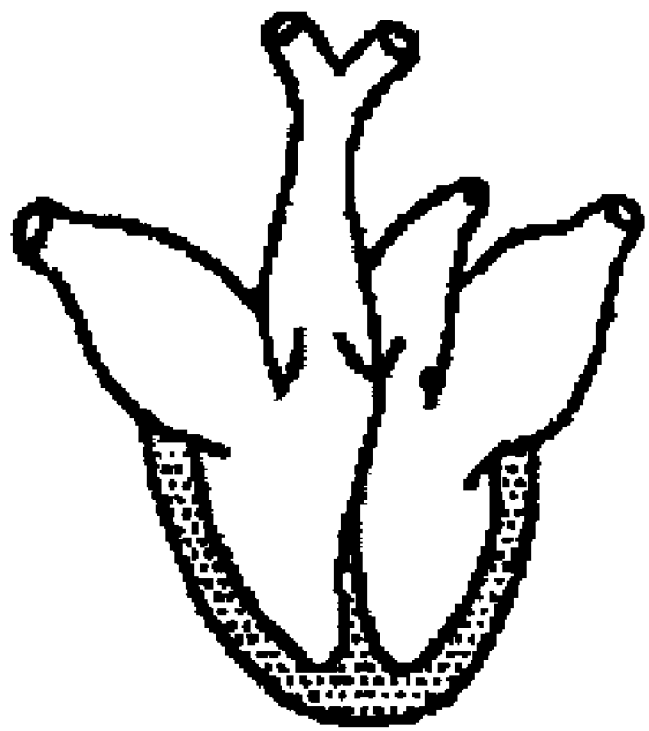
FIG. 24 is a diagram showing a mesodiastolic cardiac coronal image.

Referring back to FIG. 23, at Step S14, sectional conversion images of a cardiac coronal plane and/or its sagittal plane are image-reconstructed using the X-ray projection data acquired at Step S13. Confirmation is made as to whether the heart is placed in a predetermined cardiac phase (mesodiastole or predetermined cardiac triggered phase). At this time, confirmation is made as to whether each part of the heart such as the coronary artery is properly drawn or plotted at the coronal image and sagittal image. It is also determined whether imaging is done in the proper cardiac phase or cardiac triggered phase. Further, a decision is made as to whether the imaging is done in the proper cardiac phase or cardiac triggered phase, depending upon the degree of artifacts produced from the motion of the heart. An example of a coronal image in which the heart placed in mesodiastole is drawn properly, is shown in FIG. 24.

At Step S15, a contrast agent (iodide) is injected into an arm vein of the subject in small quantities. Thereafter, the cardiac region (main e or the like) of the subject is monitor-scanned by an intermittent scan after the elapse of a predetermined time having considered allowance prior to cardiac attainment. Further, a delay time (that is, a delay time from the injection of the contrast agent to its attainment to the main art) from image reconstruction in real time to the attainment of a CT value of a vascular portion to a predetermined value or more is determined. In the intermittent method according to the present embodiment, a low exposed dose is realized by performing a conventional scan (axial scan) of one rotation (0.35 s) of gantry at approximately one-second intervals. A monitor scan corresponding to an intermittent scan at time T1 intervals is shown in FIG. 25.

When it is found at Step S16 that the proper cardiac phase or cardiac triggered phase is taken by reference to the result of discrimination at Step S14, a routine procedure for the cardiac imaging proceeds to Step S17, where an actual injection of the contrast agent is performed again and a high-speed helical scan (actual scan) large in helical pitch is performed in timing with the predetermined cardiac phase subsequent to the elapse of the measured delay time.

Figure 25:
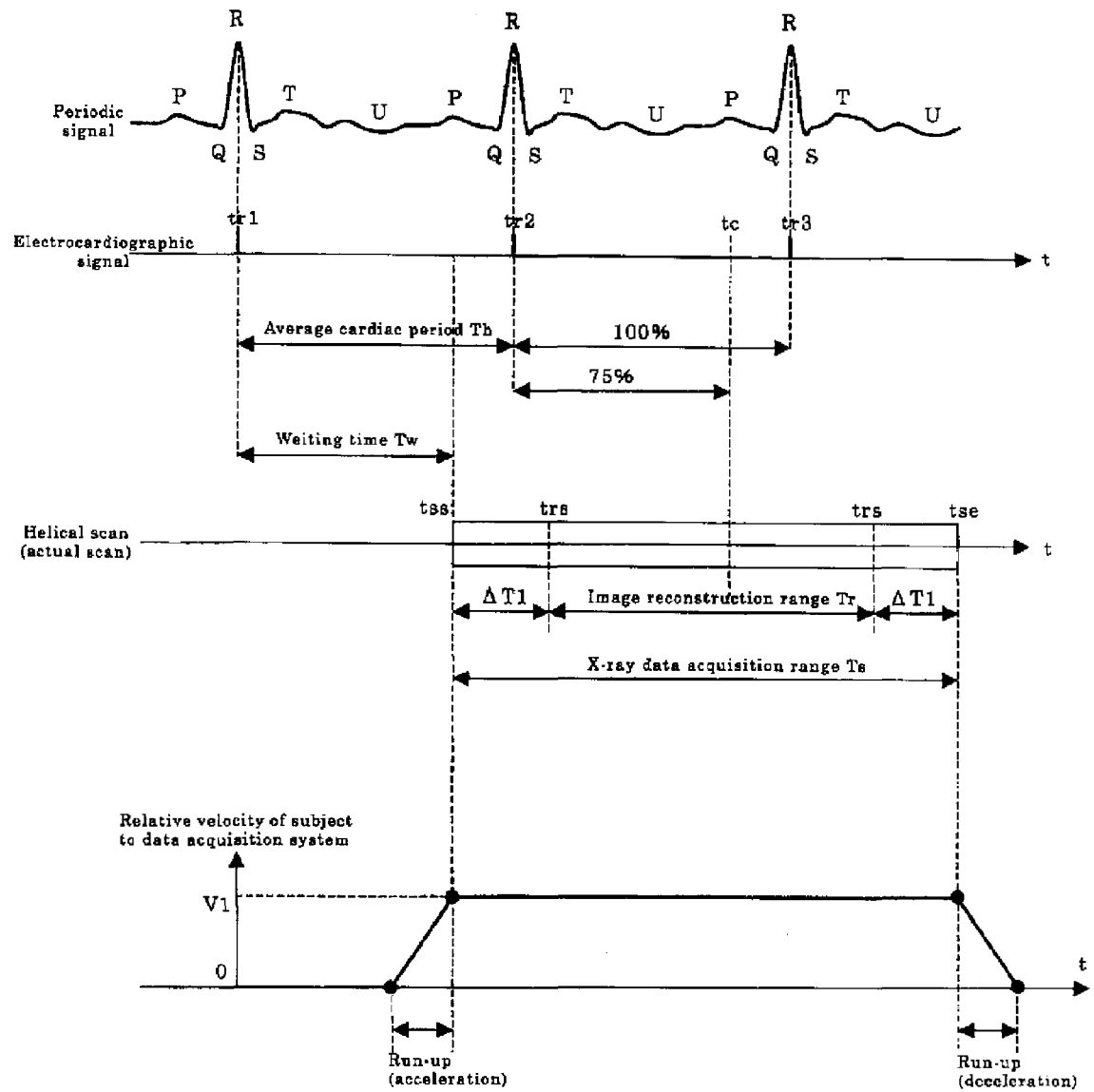
FIG. 25 is a diagram showing the relationship between a helical scan at an actual scan and a cardiac periodic signal.

FIG. 25 shows the relationship between a helical scan for an actual scan and a cardiac periodic signal.

At Step S15, the subject is returned to the predetermined position after the acquisition of the delay time, and the contrast agent is injected into the arm's vein. Further, the elapse of a contrast agent delay time is awaited. When the delay time is almost reached, the high-speed helical scan large in helical pitch is effected on the subject. The subject is conveyed to the scan start position zs by the cradle 12.

Assuming that the latest average cardiac or heartbeat period is Th (corresponding to the average of latest four cardiac periods, for example), a waiting time from a cardiac periodic signal tr1 to the start of X-ray data acquisition is Tw, an X-ray data acquisition range is [tss, tse], an image reconstruction range is [trs, tre], the time of cardiac phase 75% is tc, an X-ray data acquisition range on a time base t of the helical scan for the actual scan is Ts, an image reconstruction range on the time base t of the helical scan for the actual scan is Tr, an allowance time from the start time of the X-ray data acquisition range Ts to the start time of the image reconstruction range Tr is T1, and an allowance time from the end time of Tr to the end time of the X-ray data acquisition range Ts is T1, the following equations (Equations 22, 23, 24 and 25) are given as follows:

[Equation 22]

$$tc=(tss+tse)/2=(trs+tre)/2 \quad (22)$$

[Equation 23]

$$trs=tc-Tr/2=tss+T1 \quad (23)$$

[Equation 24]

$$tss=tc-Ts/2=trs-T1 \quad (24)$$

[Equation 25]

$$Tw=Th+tc-Ts/2 \quad (25)$$

Thus, the waiting time Tw is awaited from the cardiac periodic signal tr1 at the X-ray data acquisition start time tss and X-ray irradiation is started, after which a high-speed helical scan large in helical pitch is performed. When a cardiac region of 12 cm is helically scanned where the scan speed is 0.35 seconds per rotation, the X-ray beam width is 40 mm, and the helical pitch is 1.375, cardiac imaging can be carried out in about 0.76 seconds (=120/(40×1.375/0.35)).

If the scan speed becomes 0.2 seconds per rotation, then the cardiac imaging is enabled in about 0.43 seconds (=120/(40×1.375/0.2)).

If the scan speed is 0.35 seconds per rotation, the X-ray beam width is 80 mm, and the helical pitch is 1.375, then the cardiac imaging is made possible in about 0.38 seconds (=120/(80×1.375/0.35)).

Thus, the imaging of the whole heart is allowed at approximately one heartbeat or time not greater than it, and hence a high-speed scan can be realized.

Referring back to FIG. 23, when it is found from the discrimination at Step S16 referred to above that the appropriate cardiac phase or appropriate cardiac triggered phase has not been taken, the routine procedure proceeds to Step S18, where an electrocardiographic synchronism-based helical scan slow in helical pitch similar to the prior art is performed. Preparing this scan method is effective for a subject high in heart rate.

Incidentally, relative velocity of the subject to the data acquisition system at the helical scan is shown in graph form shown below FIG. 25. It is better that the cradle should be operated at the maximum velocity between [tss and tse] corresponding to the X-ray data acquisition range Ts. Therefore, a run-up time and a run-up distance for acceleration are determined in advance, and then the operating speed of the cradle 12 is controlled so as to reach the maximum or top velocity V1 at the time tss. When the scan gantry 20 is operated, the operating speed of the scan gantry 20 is controlled.

Figure 26:
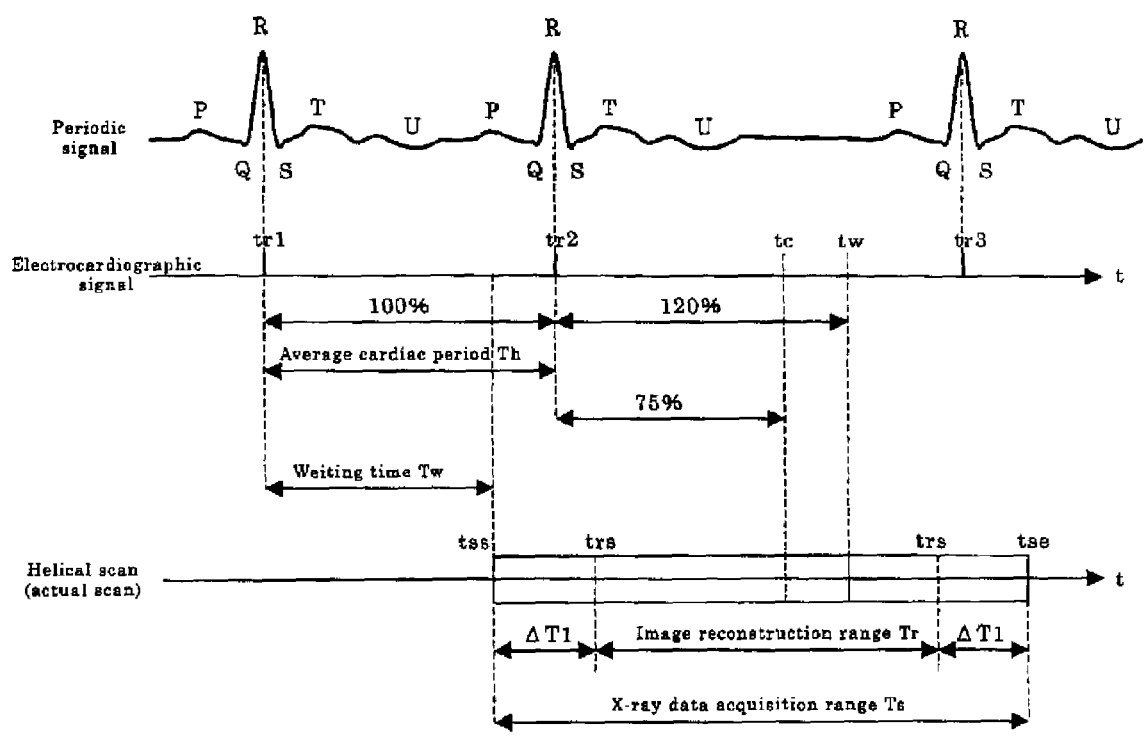
FIG. 26 is a diagram illustrating the relationship between a helical scan at an actual scan and a cardiac periodic signal where a cardiac period is made long.
Figure 27:
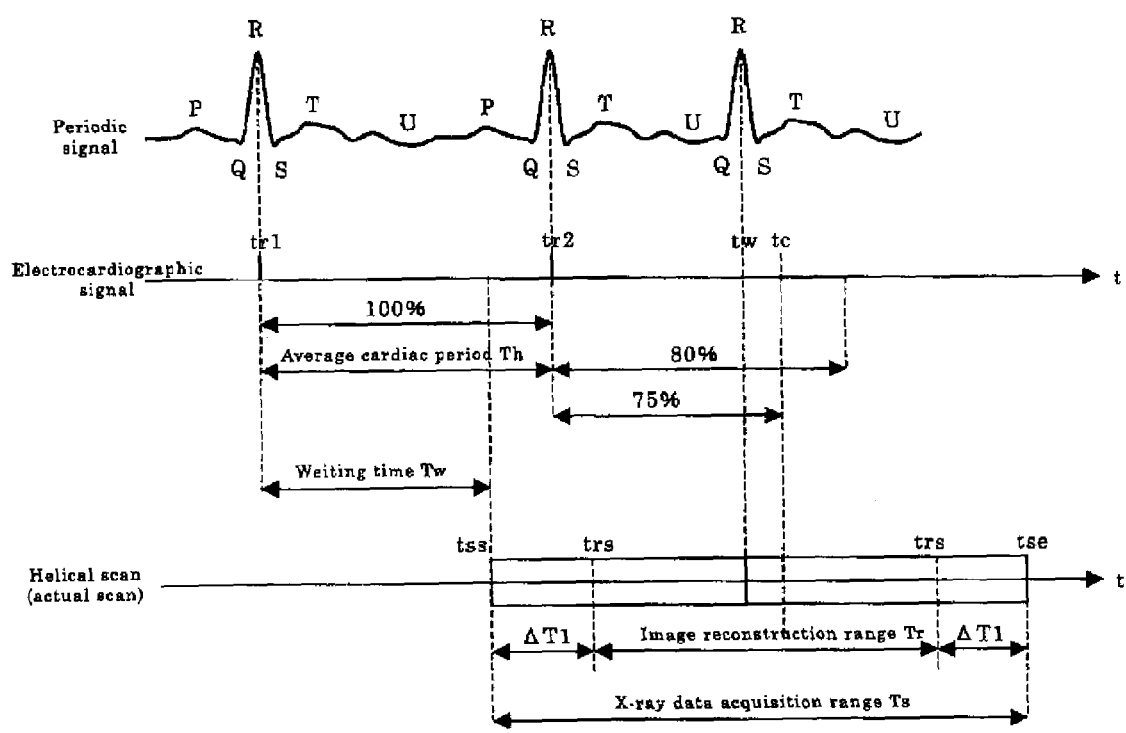
FIG. 27 is a diagram showing the relationship between a helical scan at an actual scan and a cardiac periodic signal where a cardiac period is made short.

In view of processing for arrhythmia, the relationship between a helical scan and an electrocardiographic sync signal at the time that a cardiac or heartbeat period is made long is shown in FIG. 26, and the relationship between a helical scan and an electrocardiographic sync signal at the time that a cardiac period is made short is shown in FIG. 27.

It is understood from FIG. 26 that assuming that the range allowable for an average cardiac period Th is ±20%, for example, the cardiac period is abnormal at the time of tw where a trigger signal of an electrocardiographic sync signal does not come by the time tw corresponding to 120% of the average cardiac period Th.

It is understood from FIG. 27 that assuming that the range allowable for an average cardiac period This ±20%, for example, the cardiac period is abnormal at the time of tw where a trigger signal of an electrocardiographic sync signal comes by the time tw corresponding to 80% of the average cardiac period Th.

When these abnormalities of cardiac period are found, X-ray radiation will be made stopped if possible. If it is unable to stop the X-ray radiation, X-ray projection data acquisition is performed to the end of the helical scan. In any case, the start and end points of the helical scan are reversed from this time and re-imaging can be performed again in the opposite direction. However, if arrhythmia appears seriously and the cardiac period is not stable, then the imaging can also be stopped.

Second Embodiment

Figure 28:
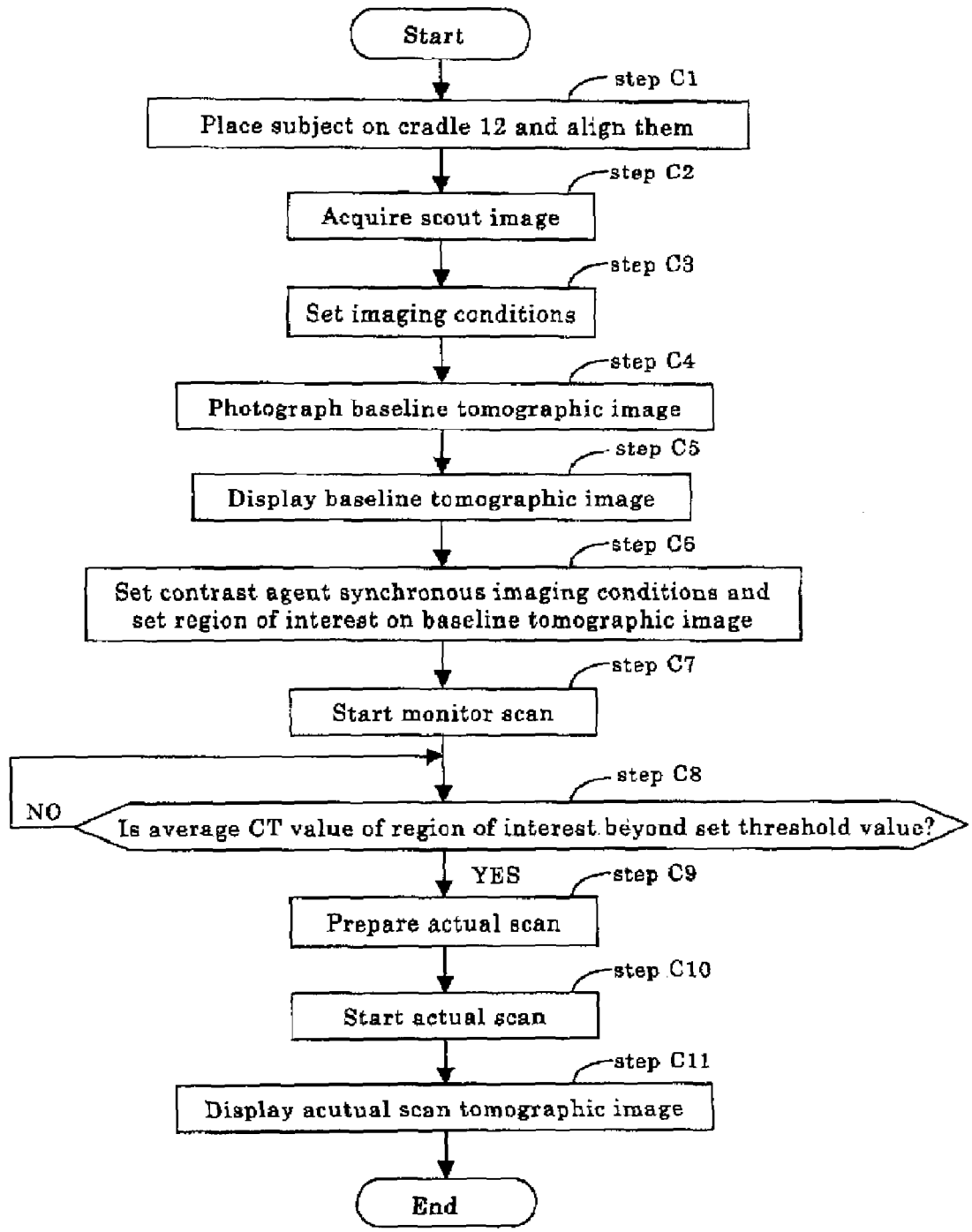
FIG. 28 is a diagram depicting the flow of a contrast agent synchronous imaging process.

A second embodiment shows an embodiment of a method illustrative of the contrast agent synchronous imaging employed in Step S15 or Step S17 shown in FIG. 23 of the first embodiment FIG. 28 shows an example of the flow of processing for the contrast agent synchronous imaging.

At Step C1, a subject is placed on the cradle 12 and they are aligned with each other.

At Step C2, scout image acquisition is performed.

At Step C3, an imaging condition setting is carried out.

At Step C4, baseline tomographic image imaging is performed.

At Step C5, a baseline tomographic image display is done.

At Step C6, a contrast agent synchronous imaging condition setting is carried out. A region-of-interest setting on a baseline tomographic image is carried out.

Figure 29:
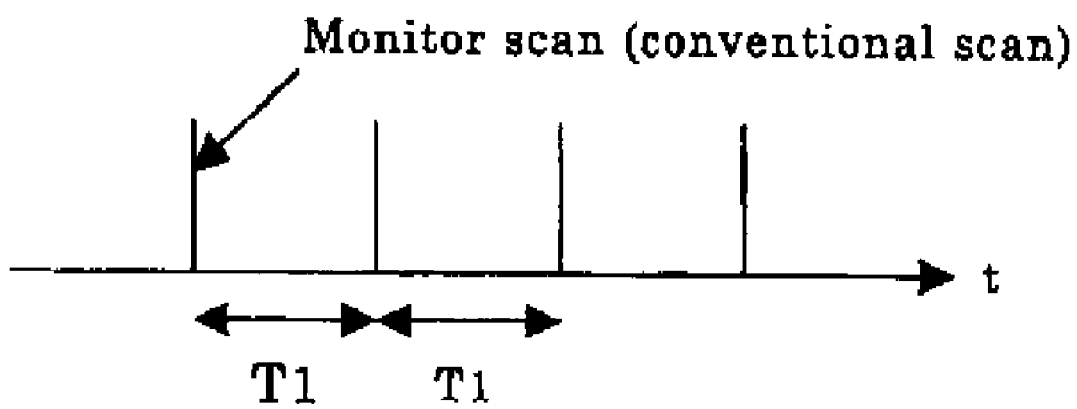
FIG. 29 is a diagram showing an intermittent scan for a monitor scan

At Step C7, a monitor scan is started. The monitor scan is shown in FIG. 29.

At Step C8, it is decided whether an average CT value in the region of interest exceeds a set threshold value. If the answer is found to be YES, then the flow of processing proceeds to Step C9. If the answer is found to be NO, then Step C8 is repeated. A delay time for the contrast agent is found from the timing at which the average CT value exceeds the threshold value.

At Step C9, preparation for an actual scan is made. The cradle 12 on the photographing table 10 is shifted to the position for the actual scan.

At Step C10, the actual scan is started

At Step C11, an actual scan tomographic image display is carried out.

Upon the baseline tomographic image photography at Step C4, the region of interest used in the monitor scan is set. If a plurality of sheets of tomographic images are photographed in the z direction at the monitor scan, then a plurality of sheets of tomographic images are photographed in the z direction even at the baseline tomographic image photography. When a plurality of regions of interest are set in the z direction, a plurality of regions of interest are set in the z direction even at the baseline tomographic image photography. If a plurality of regions of interest are set within a tomographic image in an xy plane, then a plurality of regions of interest are set to within one tomographic image at the baseline tomographic image photography.

Figure 30:
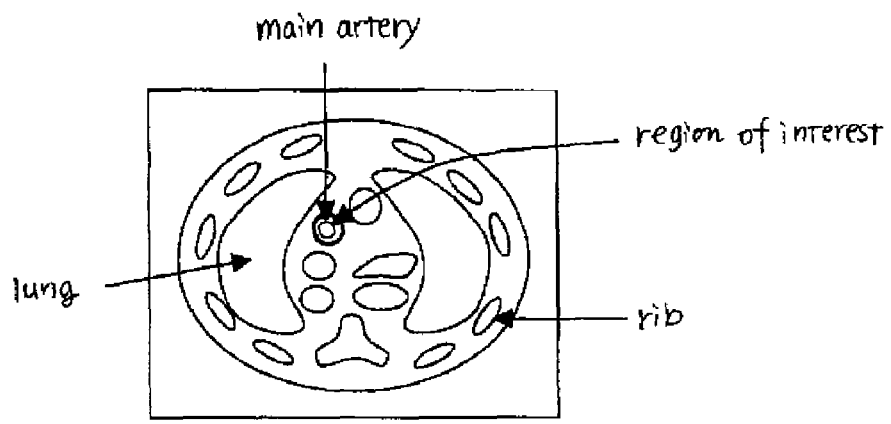
FIG. 30(a) is a diagram illustrating a baseline tomographic image.
FIG. 30(b) is a diagram showing a display example of a monitor scan for contrast agent synchronous photography.
Figure 30:
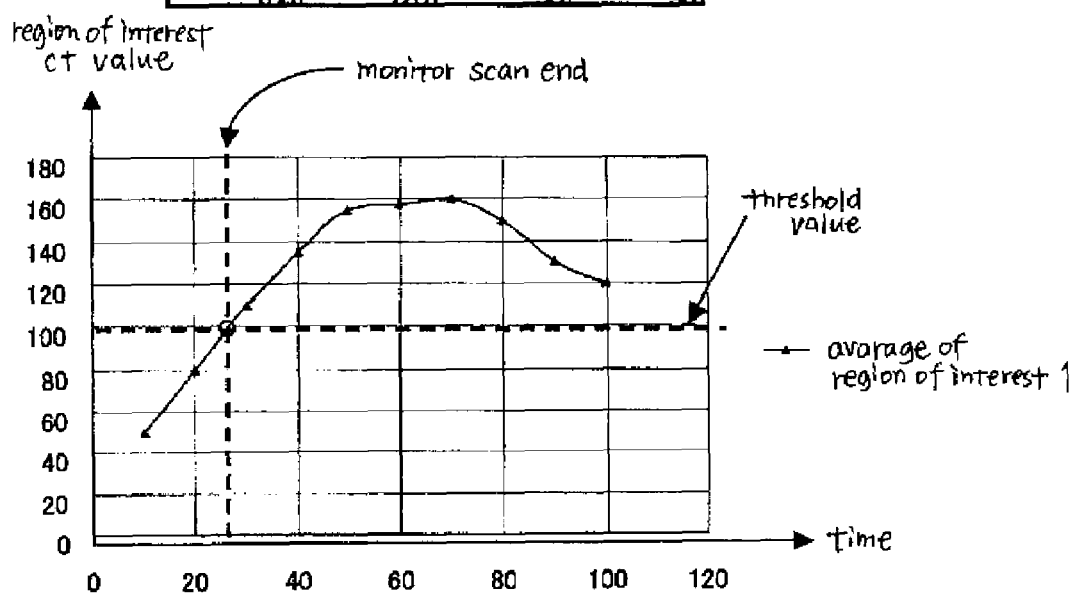

An example of a screen for the above-described contrast agent synchronous imaging is shown in FIGS. 30(a) and 30(b).

In a baseline tomographic image shown in FIG. 30(a), a region of interest 1 is set to a man artery. Tis device that a contrast agent flows and the region of interest is first set to such a main artery that a CT value increases, thereby using it as a trigger for the actual scan. A change in CT value of each region of interest ROI1 at each time t is shown in FIG. 30(b).

Assuming now that a threshold value used as for a trigger for the actual scan is set to a CT value 100 on the region of interest 1 (ROI1), a CT value on the region of interest 1 (ROI1) reaches a predetermined threshold value in a little less than about 30 seconds, so that the actual scan is triggered. At Step S17, the actual scan is triggered in this way.

At Step S15, a contrast agent delay time is outputted or displayed upon a test injection.

According to the present embodiment as described above, the imaging or photographing time can greatly be shortened by the high-speed helical scan, and the exposed dosage can greatly be reduced (to 1/5 of the conventional one). Further, a reduction in the amount of injection of the contrast agent can also be expected.

The present embodiment results in a technology essential as one heart imaging or scanning technique by an X-ray CT apparatus using a future multi-row X-ray detector or two-dimensional X-ray area detector of a matrix structure typified by a flat panel X-ray detector.

According to the X-ray CT apparatus or X-ray CT imaging method of the present invention the above-described X-ray CT apparatus 100 can bring about an advantageous effect in that it is possible to realize the photography or imaging of the heart at the low dosage and high speed and with good image quality by the helical scan, variable pitch helical scan or helical shuttle scan of the X-ray CT apparatus having the multi-row X-ray deter or the two-dimensional X-ray area detector of matrix structure typified by the flat panel X-ray detector.

Incidentally, the image reconstructing method according to the present embodiment may be a three-dimensional image reconstructing method based on the Feldkamp method known to date. Further, it may be another three-dimensional image reconstructing method. Alternatively, it may be two-dimensional image reconstruction.

Although the above embodiment has explained the example of the cardiac imaging, the present invention is not limited to it. The two coronary arteries for feeding nutrition to the heart muscle extend over the surface of the heart. The coronary arteries move greatly with the motion of the heart at the surface of the heart. Therefore, artifacts with the motion thereof are apt to occur in its tomographic image. Accordingly, the present invention brings about an effect even with resect to the photography of the coronary arteries in particular in like manner.

Although the above embodiment has described such a helical scan that the photographing table 10 is moved, the present invention can be applied even to such an X-ray CT apparatus that the scan gantry 20 is moved in the direction of the body axis of the subject in reverse.

Although the present embodiment has been described as the case in which the helical scan is used, an effect can be brought about in like manner even in the case of the variable pitch helical scan and the helical shuttle scan.

Although the present embodiment has been described as the case in which the scan gantry 20 is not tilted a similar effect can be brought about even in the case of a so-called tilt scan in which the scan gantry 20 is tilted.

In the present embodiment, the row-direction (z-direction) filters different in coefficient for every row are convoluted, thereby adjusting variations in image quality and realizing a uniform slice thickness, artifacts and the image quality of noise at each row. Although various z-direction filter coefficients are however considered therefor, any can bring about a similar effect.

Although the present embodiment has been described on the basis of the medical X-ray CT apparatus, it can be made available to an X-ray CT-PET apparatus utilized in combination with an industrial X-ray CT apparatus or another apparatus, an X-ray CT-SPECT apparatus utilized in combination therewith, etc.

The invention claimed is:

1. An X-ray CT apparatus comprising:
   an X-ray data acquisition device for acquiring X-ray projection data transmitted through a subject lying between an X-ray generator and an X-ray detector having a two-dimensional detection plane by a helical scan which acquires X-ray projection data, while said X-ray generator and said X-ray detector are being rotated about a center of rotation lying therebetween with said X-ray generator and said X-ray detector moving relative to the subject lying therebetween;
   an image reconstructing device for image-reconstructing said acquired projection data;
   an image display device for displaying an image-reconstructed tomographic image; and
   an imaging condition setting device for setting various kinds of imaging conditions for a tomographic image,
   wherein said X-ray data acquisition device includes a first device for a high pitch helical scan using a helical pitch capable for scanning a whole heart of the subject within a time of one heart-beat in synchronization with a predetermined phase in one cycle of a cardiac signal of said subject.

2. The X-ray CT apparatus according to claim 1, wherein said helical pitch capable for scanning a whole heart of the subject within a time of one heart-beat is 1 or more, wherein said helical pitch is defined by a ratio S/D, wherein D is a width of X-ray beam irradiated from said X-ray generator in relative moving direction of said X-ray generator and said X-ray detector to a subject and S is an amount of said relative movement.

3. The X-ray CT apparatus according to claim 1, wherein said X-ray data acquisition device further comprises a second device for a low pitch helical scan using a helical pitch smaller than that of the high pitch helical scan,
and said X-ray CT apparatus further comprises a selecting device for selecting one of the high pitch helical scan and the low pitch helical scan.

4. The X-ray CT apparatus according to claim 3, further comprises a deciding device for deciding whether the high pitch helical scan is possible to be properly carried out,
and said selecting device selects one of the high pitch helical scan and the low pitch helical scan based on the decision obtained by said deciding device.

5. The X-ray CT apparatus according to claim 4, wherein said deciding device includes a device for reconstructing a coronal image and/or a sagittal image based on a lower dose high pitch helical scan using an X-ray dose lower than said high pitch helical scan.

6. The X-ray CT apparatus according to claim 1, wherein said first device performs X-ray data acquisition synchronized with a predetermined phase defined by a rate relative to one cycle of said cardiac signal.

7. The X-ray CT apparatus according to claim 6, wherein said first device performs X-ray data acquisition synchronized with a predetermined phase by synchronizing a center of a helical scan range with a timing of 75±5% of one cycle later than an R wave.

8. The X-ray CT apparatus according to claim 1, wherein said first device performs X-ray data acquisition synchronized with a predetermined phase defined by an absolute time period from said cardiac signal.

9. The X-ray CT apparatus according to claim 8, wherein said first device performs X-ray data acquisition synchronized with a predetermined phase by synchronizes a center of a helical scan range with a timing 0.5 second later than an R wave.

10. An X-ray CT imaging method comprising:
an X-ray data acquisition step for acquiring X-ray projection data transmitted through a subject lying between an X-ray generator and an X-ray detector having a two-dimensional detection plane by a helical scan which acquires X-ray projection data while said X-ray generator and said X-ray detector are being rotated about a center of rotation lying therebetween with said X-ray generator and said X-ray detector moving relative to the subject lying therebetween; and
an image reconstructing step for image-reconstructing said acquired projection data;
wherein said X-ray data acquisition step includes a first step for a high pitch helical scan using a helical pitch capable for scanning a whole heart of the subject within a time of one heart-beat in synchronization with a predetermined phase in one cycle of a cardiac signal of said subject.

11. The X-ray CT imaging method according to claim 10, wherein said helical pitch capable for scanning a whole heart of the subject within a time of one heart-beat is 1 or more, wherein said helical pitch is defined by a ratio S/D, wherein D is a width of an X-ray beam irradiated from said X-ray generator in relative moving direction of said X-ray generator and said X-ray detector to a subject and S is an amount of said relative movement.

12. The X-ray CT imaging method according to claim 10, wherein said X-ray data acquisition step further comprises a second step for a low pitch helical scan using a helical pitch smaller than that of the high pitch helical scan,
and said X-ray CT imaging method further comprises a selecting step for selecting one of the high pitch helical scan and the low pitch helical scan.

13. The X-ray CT imaging method according to claim 12, further comprises a deciding step for deciding whether the high pitch helical scan is possible to be properly carried out,
and said selecting step includes selecting one of the high pitch helical scan and the low pitch helical scan based on the decision obtained by said deciding device.

14. The X-ray CT imaging method according to claim 13, wherein said deciding step includes a step for reconstructing a coronal image and/or a sagittal image based on a lower dose high pitch helical scan using an X-ray dose lower than said high pitch helical scan.

15. The X-ray CT imaging method according to claim 10, wherein said first step includes performing an X-ray data acquisition synchronized with a predetermined phase defined by a rate relative to one cycle of said cardiac signal.

16. The X-ray CT imaging method according to claim 15, wherein said first step performs X-ray data acquisition synchronized with a predetermined phase by synchronizing a center of a helical scan range with a timing of 75±5% of one cycle later than an R wave.

17. The X-ray CT imaging method according to claim 10, wherein said first step performs X-ray data acquisition in synchronization with a predetermined phase defined by an absolute time period from said cardiac signal.

18. The X-ray CT imaging method according to claim 17, wherein said first step performs X-ray data acquisition in synchronization with a predetermined phase by synchronizing a center of a helical scan range with a timing 0.5 second later than an R wave.

* * * * *